US009125581B2

(12) United States Patent
Wu et al.

(10) Patent No.: US 9,125,581 B2
(45) Date of Patent: Sep. 8, 2015

(54) CONTINUOUS MODELING FOR DIPOLE LOCALIZATION FROM 2D MCG IMAGES WITH UNKNOWN DEPTH

(75) Inventors: Chenyu Wu, Mountain View, CA (US); Jing Xiao, Cupertino, CA (US)

(73) Assignee: Seiko Epson Corporation, Tokyo (JP)

( * ) Notice: Subject to any disclaimer, the term of this patent is extended or adjusted under 35 U.S.C. 154(b) by 688 days.

(21) Appl. No.: 13/478,682

(22) Filed: May 23, 2012

(65) Prior Publication Data
US 2013/0317337 A1    Nov. 28, 2013

(51) Int. Cl.
*A61B 5/05*    (2006.01)
*A61B 5/04*    (2006.01)

(52) U.S. Cl.
CPC ............... *A61B 5/05* (2013.01); *A61B 5/04007* (2013.01); *A61B 5/04008* (2013.01); *A61B 2576/023* (2013.01)

(58) Field of Classification Search
CPC .................................. A61B 5/05; A61B 5/055
USPC ................................................... 600/407, 409
See application file for complete search history.

(56) References Cited

U.S. PATENT DOCUMENTS

| | | | |
|---|---|---|---|
| 7,395,107 B2* | 7/2008 | Ishiyama et al. | 600/409 |
| 2012/0197145 A1* | 8/2012 | Wu et al. | 600/509 |
| 2012/0219195 A1* | 8/2012 | Wu et al. | 382/128 |
| 2013/0324832 A1* | 12/2013 | Wu et al. | 600/409 |

OTHER PUBLICATIONS

Georgopoulos, E.F., et al., "Human MagnetoCardioGram (MCG) modeling using Evolutionary Artificial Neural Networks", Combinations of Evolutionary Computation and Neural Networks, 2000 IEEE Symposium, May 2000, pp. 110-120.
Jiang, S., et al., "ANN Interpolation in MCG Mapping", Proceedings of the 2005 IEEE Engineering in Medicine and Biology 27th Annual Conference, Sep. 1-4, 2005.

* cited by examiner

*Primary Examiner* — Peter Luong

(57) ABSTRACT

A system identifies double-layer dipoles in a magnetic image by defining two-dimensional patches of distributed point charges that simulate the double-layer dipoles. The geometric center of a two-dimensional patch is used as the location of an equivalent dipole moment of the double-layer dipole. The momentum of the equivalent dipole moment is determined by submitting the magnetic image to a dipole construction system that identifies the location and momentum based on the submitted magnetic image.

19 Claims, 24 Drawing Sheets

Example of a healthy Person

Example of mayocardial infarction

Strong

Current Strength

Weak

Point Current Sink

Point Current Source $id$
(Dipole Moment)

MCG Image Difference
Symmetrical Sources
Vertical Patch (X × Z)

| Size of Sources | Max MCG | Min MCG | Max Error (%) | Min Error (%) |
|---|---|---|---|---|
| 1 × 1 | 1.006e-10 | -1.006e-10 | 0 | 0 |
| 3 × 3 | 9.056e-10 | -9.056e-10 | 0.028 | 0 |
| 5 × 5 | 2.518e-9 | -2.518e-9 | 0.084 | 0 |
| 7 × 7 | 4.941e-9 | -4.941e-9 | 0.168 | 0 |
| 9 × 9 | 8.181e-9 | -8.181e-9 | 0.282 | 0 |
| 11 × 11 | 1.225e-8 | -1.225e-8 | 0.424 | 0 |
| 13 × 13 | 1.715e-8 | -1.715e-8 | 0.598 | 0 |
| 15 × 15 | 2.289e-8 | -2.289e-8 | 0.803 | 0 |

FIG. 17

MCG Image Errors
Symmetrical Sources
Horizontal Patch (X × Y)

| Size of Sources | Max MCG | Min MCG | Max Error (%) | Min Error (%) |
|---|---|---|---|---|
| 1 × 1 | 7.693e-11 | -7.693e-11 | 0 | 0 |
| 3 × 3 | 6.920e-10 | -6.920e-10 | 0.029 | 0 |
| 5 × 5 | 1.920e-9 | -1.920e-9 | 0.087 | 0 |
| 7 × 7 | 3.755e-9 | -3.755e-9 | 0.173 | 0 |
| 9 × 9 | 6.192e-9 | -6.192e-9 | 0.287 | 0 |
| 11 × 11 | 9.220e-9 | -9.220e-9 | 0.427 | 0 |
| 13 × 13 | 1.283e-8 | -1.283e-8 | 0.594 | 0 |
| 15 × 15 | 1.700e-8 | -1,700e-8 | 0.785 | 0 |
| 17 × 17 | 2.173e-8 | -2.173e-8 | 0.999 | 0 |
| 19 × 19 | 2.698e-8 | -2.698e-8 | 1.235 | 0 |
| 21 × 21 | 3.275e-8 | -3.275e-8 | 1.491 | 0 |

Dipole Localization Errors Compared to Geometric Center
(Vertical Patch, 150 Trials)

| Size of Symmetrical Sources | Error (mm) | Size of Asymmetrical Sources (XxZ) | Error (mm) |
|---|---|---|---|
| 1 × 1 | 1.347 +/- 0.945 | 1 × 3 | 1.424 +/- 0.724 |
|  |  | 3 × 1 | 1.237 +/- 0.774 |
| 3 × 3 | 1.313 +/- 0.790 | 3 × 5 | 1.250 +/- 0.834 |
|  |  | 5 × 3 | 1.199 +/- 0.623 |
| 5 × 5 | 1.261 +/- 0.754 | 5 × 7 | 1.188 +/- 0.610 |
|  |  | 7 × 5 | 1.149 +/- 0.706 |
| 7 × 7 | 1.140 +/- 0.597 | 7 × 9 | 1.016 +/- 0.588 |
|  |  | 9 × 7 | 1.269 +/- 0.635 |
| 9 × 9 | 1.115 +/- 0.598 | 9 × 11 | 1.163 +/- 0.639 |
|  |  | 11 × 9 | 1.059 +/- 0.639 |
| 11 × 11 | 1.173 +/- 0.753 | 11 × 13 | 1.173 +/- 0.753 |
|  |  | 13 × 11 | 1.040 +/- 0.585 |
| 13 × 13 | 1.040 +/- 0.585 | 13 × 15 | 1.013 +/- 0.608 |
|  |  | 15 × 13 | 1.141 +/- 0.707 |
| 15 × 15 | 0.958 +/- 0.592 |  |  |

Dipole Localization Errors Compared to Geometric Center
(Horizontal Patch, 200 Trials)

| Size of Symmetrical Sources | Error (mm) | Size of Asymmetrical Sources (X × Y) | Error (mm) |
|---|---|---|---|
| 1 × 1 | 1.542 +/- 0.889 | 1 × 3 | 1.658 +/- 1.147 |
|  |  | 3 × 1 | 1.648 +/- 1.280 |
| 3 × 3 | 1.261 +/- 0.829 | 3 × 5 | 1.586 +/- 1.251 |
|  |  | 5 × 3 | 1.419 +/- 0.961 |
| 5 × 5 | 1.542 +/- 0.939 | 5 × 7 | 1.239 +/- 0.893 |
|  |  | 7 × 5 | 1.338 +/- 0.966 |
| 7 × 7 | 1.332 +/- 0.977 | 7 × 9 | 1.404 +/- 1.052 |
|  |  | 9 × 7 | 1.365 +/- 1.175 |
| 9 × 9 | 1.317 +/- 0.970 | 9 × 11 | 1.357 +/- 1.046 |
|  |  | 11 × 9 | 1.324 +/- 0.886 |
| 11 × 11 | 1.415 +/- 1.080 | 11 × 13 | 1.453 +/- 1.005 |
|  |  | 13 × 11 | 1.414 +/- 1.007 |
| 13 × 13 | 1.468 +/- 1.039 | 13 × 15 | 1.556 +/- 1.182 |
|  |  | 15 × 13 | 1.460 +/- 1.052 |
| 15 × 15 | 1.458 +/- 1.062 | 15 × 17 | 1.379 +/- 1.088 |
|  |  | 17 × 15 | 1.626 +/- 1.110 |
| 17 × 17 | 1.474 +/- 0.989 | 17 × 19 | 1.498 +/- 1.084 |
|  |  | 19 × 17 | 1.539 +/- 1.133 |
| 19 × 19 | 1.627 +/- 1.087 | 19 × 21 | 1.474 +/- 1.229 |
|  |  | 21 × 19 | 1.605 +/- 1.058 |
| 21 × 21 | 1.484 +/- 1.067 |  |  |

FIG. 22

$$\vec{B}(\vec{r_m}) = \frac{\mu_0}{4\pi} \frac{\vec{J}(\vec{p}) \times (\vec{r_m} - \vec{p})}{\|\vec{r_m} - \vec{p}\|^3}, m = 1 \cdots M \qquad \text{Eq. 1}$$

$$B_z(\vec{r_m}) = \frac{\mu_0}{4\pi} \frac{[-J^2, J^1] \cdot [r_m^1 - x_p, r_m^2 - y_p]'}{[(r_m^1 - x_p)^2 + (r_m^2 - y_p)^2 + (r_m^3 - z_p)^2]^{3/2}} \qquad \text{Eq. 2}$$

$$B_z^m(z) = \frac{a_m}{[b_m + (c-z)^2]^{3/2}} \qquad \text{Eq. 3}$$

$$B_z^m(z + \Delta z) \qquad \text{Eq. 4}$$
$$= B_z^m(z) + \frac{d}{dz} B_z^m(z) \cdot \Delta z + \frac{d^2}{2dz} B_z^m(z) \cdot \Delta z^2 + O(\Delta z^3)$$

$$B_{xy}(i,j) = \sqrt{(\partial B_z(i,j)/\partial x)^2 + (\partial B_z(i,j)/\partial y)^2} \qquad \text{Eq. 5}$$

$$\vec{B^m} = \vec{J} \times \vec{R_m} = -\vec{R_m} \times \vec{J} \qquad \text{Eq. 6}$$

where $\vec{B^m} = \vec{B}(\vec{r_m})$, $\vec{J} = \vec{J}(\vec{p})$ and $\vec{R_m} = \frac{\mu_0}{4\pi} \frac{(\vec{r_m} - \vec{p})}{\|\vec{r_m} - \vec{p}\|^3}$.

FIG. 26A

$$\vec{B^m} = -[\vec{R_m}]_\times \vec{J}$$
$$= -\begin{bmatrix} 0 & -R_m^3 & R_m^2 \\ R_m^3 & 0 & -R_m^1 \\ -R_m^2 & R_m^1 & 0 \end{bmatrix} \cdot \begin{bmatrix} J^1 \\ J^2 \\ J^3 \end{bmatrix} \quad\quad Eq.\ 7$$

$$B_z^m = \begin{bmatrix} R_m^2, & -R_m^1 \end{bmatrix} \cdot [J^1, J^2]' \quad\quad Eq.\ 8$$

$$\underbrace{\begin{bmatrix} B_z^1 \\ B_z^2 \\ \vdots \\ B_z^M \end{bmatrix}}_{\mathbf{B}} = \underbrace{\begin{bmatrix} R_1^2 & -R_1^1 \\ R_2^2 & -R_2^1 \\ \vdots & \vdots \\ R_M^2 & -R_M^1 \end{bmatrix}}_{\mathbf{R}} \cdot \underbrace{\begin{bmatrix} J^1 \\ J^2 \end{bmatrix}}_{\mathbf{J}} \quad\quad Eq.\ 9$$

$$\mathbf{J} = (\mathbf{R}^T \mathbf{R})^{-1} \mathbf{R}^T \mathbf{B} \quad\quad Eq.\ 10$$

$$\vec{B^m} = \frac{\mu_0}{4\pi} \frac{\vec{J} \times ((\vec{r_0} + \vec{\delta_m}) - \vec{p})}{\|(\vec{r_0} + \vec{\delta_m}) - \vec{p}\|^3} = \frac{\mu_0}{4\pi} \frac{\vec{J} \times (\vec{\epsilon_0} + \vec{\delta_m})}{\|\vec{\epsilon_0} + \vec{\delta_m}\|^3} \quad\quad Eq.\ 11$$

FIG. 26B

$$\alpha \vec{B^m} = \frac{\vec{J} \times \vec{\epsilon_0} + \vec{J} \times \vec{\delta_m}}{\|\vec{\epsilon_0} + \vec{\delta_m}\|^3} \qquad Eq.\ 12$$

$$\alpha B_z^m + \frac{-J^2 x_\epsilon + J^1 y_\epsilon + \tau_m^3}{((x_\epsilon + \delta_m^1)^2 + (y_\epsilon + \delta_m^2)^2 + (z_\epsilon + \delta_m^3)^2)^{3/2}} \qquad Eq.\ 13$$
$$= f^m(x_\epsilon, y_\epsilon, z_\epsilon) = 0$$

$$z = d/\sqrt{2},\ \|\vec{J}\| = \frac{4\pi d^2 B_z^{max}}{0.385 \mu_0} \qquad Eq.\ 14$$

FIG. 26C

CONTINUOUS MODELING FOR DIPOLE LOCALIZATION FROM 2D MCG IMAGES WITH UNKNOWN DEPTH

BACKGROUND

1. Field of Invention

The invention relates to magnetic imaging of live tissue. More specifically, it relates to the identifying and locating of double-layer using magnetic images.

2. Description of Related Art

Electric current source estimation is a common problem in various electromagnetic imaging technologies. One area of electromagnetic imaging is the imaging of electric fields emanating from living tissue. Living organisms generate electric impulses, which result in electric fields, and electric imaging (or electric field imaging) makes it possible to capture images of these electric fields (hereinafter termed electric images). Ideally, one would like to reconstruct an electric impulse from its captured electric field. Electric imaging has found wide application in the medical field.

As it is known in the art, an electric current generates a magnetic field. Thus, organisms that generate electric impulses also generate magnetic fields, and magnetic imaging (or magnetic field imaging) makes it possible to capture images of these magnetic fields (hereinafter termed magnetic images). The study of such magnetic fields in living organisms, or living tissue, is generally known as biomagnetism. Of particular interest in the field of biomagnetism is the magnetic imaging of the human brain and the human heart.

The development of electric imaging and magnetic imaging technology permits the detection and analysis of electrophysiological processes in the brain, heart and other nerve systems. Recording (i.e. imaging) of the electromagnetic fields from such tissues is typically accomplished by placing multiple electric (field) sensors or magnetic (field) sensors around the tissue being studied. For example, electroencephalography (EEG) uses electric sensors placed around the brain to record electric images of brain tissue, and electrocardiography (ECG or EKG) uses electric sensors placed over the chest to record electric images of heart tissue. Similarly, magnetoencephalography (MEG) uses magnetic sensors placed around the brain to record magnetic images of brain tissue, and magnetocardiography (MCG) uses magnetic sensors placed over the chest to record magnetic images of heart tissue. Examples of an MEG unit and an MCG unit are illustrated in FIGS. 1A and 1B, respectively.

With reference to FIG. 1A, an MEG system consists of a large number (usually 300 or less) of magnetic sensors arranged in a spherical shape (to be fitted around a human head) to provide a high spatial resolution for measurements. The MEG system measures magnetic fields created by brain nerve activity. Each magnetic sensor measures a one-dimensional (1D) magnetic waveform, Bz, in the radial direction.

With reference to FIG. 1B, an MCG system may include a small number (usually 64 or fewer) of magnetic sensors (each sensor is typically a Superconducting Quantum Interference Device, or SQUID) arranged as a sensor planar array. Each SQUID sensor measures a one-dimensional (1D) magnetic waveform (Bz) in the z direction, as illustrated by (x, y, z) axes. The MCG device is usually placed above and within 10 cm of a patient's chest in a location over the patient's heart. Electric current [i.e. electric impulse(s)] in the heart generates a magnetic field B that emanates out from the patient's torso. Each SQUID sensor measure the z-component (i.e. Bz) of the emanating magnetic field B that reaches it. That is, each SQUID sensor measures a 1D magnetic waveform in the z direction.

Compared to electric imaging (or recording) technology such as EEG and ECG, magnetic imaging technology such as MEG and MCG would be preferred due it being more non-invasive and providing a two-dimensional (2D) image (by virtual of the x-y plane of SQUID sensors) at a given point in time. Moreover, the magnetic field generated outside of the human body is not distorted in the direction perpendicular to the body surface (e.g. the radial direction in FIG. 1A and the z-direction in FIG. 1B), due to the magnetic property of body tissue. Thus magnetic imaging is more accurate and sensitive to weak electric activity within the body.

By way of example, the following discussion focuses on magnetic imaging of heart tissue, but it is to be understood that the following discussion is also applicable to magnetic imaging in general, and in particular, applicable to magnetic imaging of other living tissues.

Cardiac electric currents (or current impulses) are generated by electrophysiological processes in the heart. Localization of abnormal electric currents may be used in the diagnosing of ischemic diseases such as myocardial infarction, angina cordis, etc. It also benefits patients in the catheter lab for both treatment and follow-up, as is explained in "Forty Years of Magnetocardiology", by F. Stroink, in Int. Conf. on Biomagnetism Advances in Biomagnetism, 28:1-8, 2010.

Traditionally, irregular cardiac electric activity, such as arrhythmia, is diagnosed by means of an electrocardiogram (ECG). However, an ECG only provides temporal information, and thus cannot localize abnormal electric impulse currents in the heart directly, even if the ischemic disease has been detected. One technique to attempt to localize electrical impulse currents is known as Body Surface Potential Mapping (BSPM), which uses a large number of electrodes (i.e., leads) to reconstruct a body surface potential map. This BSPM technique is explained in "Noninvasive Volumetric Imaging of Cardiac Electrophysiology", by Wang et al., in CVPR, pages 2176-2183, 2009. The accuracy of BSPM electric current localization, however, is limited because the observed electrical signals can be distorted by the poor conductivity of body tissue.

The advent of the magnetocardiogram, or magnetocardiography, (MCG) made available more accurate measurements of cardiac electric currents, both spatially and temporally. An MCG is described above in reference to FIG. 1B.

In an MCG system, electromagnetic sensors (i.e. SQUID sensor) are arranged as a sensor planar array. Each electromagnetic sensor is a capture point, and hereinafter may be referred to as a "capture". Each capture measures a 1D magnetic waveform in a direction perpendicular to the sensor planar array (i.e. the z-direction) emanating from the patient's chest (i.e. human torso). By aligning (or synchronizing) the depth measures (i.e. the 1D magnetic waveform) of the planar array of captures at a given depth in the z-direction (which may define an observation plane through the heart tissue), a 2D MCG map at the given depth may be constructed. The MCG system is usually placed five to ten centimeters above the patient's chest, and measures the patient's heart magnetic field in a non-invasive manner. Thus, the array of captures measure a collection of low resolution (hereinafter, low-res), two-dimensional MCG maps (or images) of electromagnetic activity.

MCG has a few advantages over ECG. First, the magnetic field generated by the heart's electric current impulses (hereinafter, currents, electric currents or electrical currents) is not distorted in the direction perpendicular to the body surface (i.e., the z direction), due to the magnetic property of body tissue. Thus MCG is more accurate and sensitive to weak electric activity in the early stage of heart disorders. Second, the MCG sensor array can localize the position of electric currents in the heart. Finally, MCG measurements are non-invasive. After forty years of research in MCG, cardiac electric current localization and high resolution visualization for MCG measurements are attracting more and more interest from both research and clinical areas.

However, there are a number of difficulties associated with MCG. A first difficulty is the great amount of electromagnetic noise that can obscure the small magnetic fields created in a human heart. This has been addressed, to some extent, by using a magnetically-shielded room to reduce background noise and by the introduction of a sensitive electromagnetic sensor, such as the superconducting quantum interference device (SQUID). Although these steps have helped, the raw readings nonetheless remain more noisy than desired.

Another difficulty is the limited number of electromagnetic sensors (i.e. SQUIDs) that may be used in an MCG system, which limits the resolution of an MCG map. As a result, the MCG system can typically produce only low resolution (low-res) 2D MCG maps. Typically, these low-res 2D MCG maps are not sufficient for diagnosis purposes. For example, a 64 channel Hitachi™ MCG system with a 25 mm sensor interval (as described in "Newly Developed Magnetocardiographic System for Diagnosing Heart Disease", by Tsukada et al., in Hitachi Review, 50(1):13-17, 2001) only measures an 8×8 MCG map (i.e. it has an 8×8 array of 64 measurement points, or captures). One solution is to increase the number of sensors, but this is very difficult in practice due to the physical size of the sensors and system design.

One approach to overcoming this physical limitation is to approximate a high-resolution (hereinafter, high-res) magnetic image from the low-res image created by the limited number of magnetic sensors. Thus, a necessary step in MCG is generating a high-res, 2D MCG image, or map, from a low-res, 2D MCG image, or map.

Two image examples, L and R, of high-res 2D MCG images generated from low-res images are shown in FIG. 2. Left image L shows the tangential image of a generated high-res MCG image of a healthy heart. The maximal point (i.e. strongest point) within image L indicates the location (or source) of electric current in the heart. Thus, high-res MCG images permits doctors to directly "see" the electrical activity in the heart. Right image R shows the tangential image of a high-res MCG image of an unhealthy heart. It differs significantly from left image L of a healthy heart, and thus provides important cues for diagnosis. Compared to low-res MCG maps, high-res MCG images provide more diagnostic significance.

One way to generate a high-res magnetic field image from a low-res magnetic image is by interpolation. Most modern MCG systems use curve fitting interpolation methods between observed measurements of the electromagnetic sensors to construct high-res 2D MCG images from the low-res 2D MCG maps, such as described in "Magnetocardiographic Localization of Arrhythmia Substrates: A Methodology Study With Accessory Path-Way Ablation as Reference", by B. A. S. et al., in Ann Noninvasive Electrocardiol, 10(2):152-160, 2005, and described in "Evaluation of an Infarction Vector by Magnetocardiogram: Detection of Electromotive Forces that Cannot be Deduced from an Electrocardiogram", by Nomura et al, in Int. Congress Series, 1300:512-515, 2007. Unfortunately, the accuracy of curve fitting methods is typically limited.

Recently machine learning techniques have been used for high-res magnetic field image generation. An example is presented in Interpolation in MCG Mapping, IEEE Engineering in Medicine and Biology 27th Annual Conference, Shanghai, China, pages 4381-4384, 2005, S. Jiang et al. This approach illustrates learning nonlinear interpolation functions using neural networks.

As described above, magnetic imaging provides images of the electric field at a given time and depth within a tissue. Oftentimes, it would be beneficial to identify the electric current impulse (or current impulse) responsible for the observed magnetic field. In the high-res images described above (see FIG. 2, for example) one may identify the maximal point (i.e. strongest point) within a magnetic image as being indicative of the location (or source) of a current impulse.

Trying to identify the current impulse that generated an observed magnetic image is termed the inverse problem. That is, using the obtained magnetic field measurements at different sites, one attempts to estimate the location and moment of the current source that generated the observed (i.e. the measured) magnetic field. This is called the inverse problem. For example, Conversion of Magnetocardiographic Recordings Between Two Different Multichannel Squid Devices, IEEE Trans. on Biomedical Engineering, 47(7):869-875, 2000, by M. B. et al. describes tackling the inverse problem to reconstruct the 3D position, magnitude and orientation of current sources. Once the current source is known, the high-res magnetic field can be computed from the reconstructed current source by use of the Biot-Savart law. However, due to its poor initiation, this approach is often unreliable.

There are a number of other difficulties involved in addressing the inverse problem. According to the Helmholtz reciprocity principal, the inverse problem for MCG is an ill-posed problem unless the prior electric currents and their number are known. Nonetheless, several approaches towards addressing the inverse problem have been proposed.

For example, a trivia case that assumes a single electric current located at the world origin and far from the sensor array is described in Magnetocardiographic Localization of Arrhythmia Substrates: a Methodology Study with Accessory Pathway Ablation as Reference, Europace, 11(2):169-177, 2009, R. J. et al. This situation cannot be satisfied in practice.

In the case of estimating a large number of current sources, such as estimating nerve activity in the brain, the inverse problem can be put under constraints, such as describe in Magnetic Source Images Determined by a Lead-Field Analysis The Unique Minimum-Norm Least-Squares Estimation, IEEE Trans. Biomed Eng., 39(7):665-675, 1992, by J. Z. Wang et al. This approach requires solving a large scale non-linear optimization problem, which is often computationally expensive and may lead to undesired local optima without good initialization.

Alternatively, by considering the temporal information and signal-to-noise ratio, the inverse problem can by addressed by the beam-former and synthetic aperture magnetometery (SAM) methods, as described in MEG Inverse Problem with Leadfields, 15th Japan Biomagnetism Conference, 13(1):42-45, 2000, by A. Matani. These types of methods require a statistical analysis of specific current sources, and thus do not permit the use of a one-time, 2D magnetic field image without any assumptions on current sources.

Thus, addressing the inverse problem usually requires that it be simplified by making use of regularization methods (as described by Matani, above) and that the position of current sources be given a priory (as described in An Optimal Constrained Linear Inverse Method for Magnetic Source Imaging, Nuclear Science Symposium and Medical Imaging Conference, pages 1241-1245, 1993, by P. Hughett).

However, linear solutions to the inverse problem can be approximated in special cases where the current positions are fixed at uniform 3D grids, as put forth by J. Z. Wang et al. (cited above) and in Simulation Studies of Biomagnetic Computed Tomography, IEEE Trans. Biomed Eng., 40(4):317-322, 1993, C. Ramon et al.

C. Ramon et al. also show that the inverse problem can have over-constraints in the case of a single current source, which is popularly used in many applications of heart diseases diagnosis. But even in this case, the inverse problem is still a medium-scale nonlinear optimization process, which highly depends on the initialization and the number of independent constraints. However, the sparse magnetic measurement can only provide limited information for estimating good initialization and solving the inverse problem. For example, the 64-channel Hitachi MCG system described above only measures magnetic fields on an 8×8 grid with a 25 mm sensor interval.

As it would be understood, a captured magnetic image is likely comprised of a combination of multiple electric impulses at different depths, and not the result of a single electric current impulse. What is needed is a magnetic imaging system capable of providing information relating the composite of a plurality of electric impulses responsible for an observed magnetic field.

Also needed is a magnetic imaging system that provides a view of such combinations of electric impulses without placing impractical demands on computing resources or requiring a priori assumptions regarding the number and location of previous electric currents.

SUMMARY OF INVENTION

The above needs are met in a method of identifying a double-layer dipole from a magnetic image, the method including: obtaining a magnetic image of a magnetic field generated by a double-layer dipole, wherein the double-layer dipole is of undefined shape, size, depth and orientation; submitting the magnetic image to a current dipole constructing system to determine a 3D position and momentum of an electric current in accord with the magnetic image; assigning the 3D position of the electric current to the geometric center of a single double-layer 2D patch; and deeming the geometric center of the single double-layer 2D patch to the position of an equivalent dipole moment of the double-layer dipole, the equivalent dipole moment being characterized by the generation of an electric field substantially similar to that produced by the double-layer dipole.

Preferably, the momentum generated by the dipole generator is assigned to the equivalent dipole moment.

In this case, the single double-layer 2D patch is an approximation of the double-layer dipole.

Preferably, the single double-layer 2D patch is of undefined size.

Additionally, the double-layer 2D patch is a distribution of point sources of electric charge having a common polarity.

Also, the single double-layer 2D patch defines an isochronal activation surface.

Additionally, the single double-layer 2D patch is one of two opposing surfaces that define the equivalent double-layer dipole, the equivalent double-layer dipole being equivalent to the double-layer dipole whose magnetic field is represented in the magnetic image.

Also in this method, the electric field produced by the equivalent dipole moment is substantially similar to that produced by the double-layer dipole when viewed from a distance of multiple times the diameter of the surface of the double-layer dipole.

In a preferred embodiment, the magnetic image of the magnetic field generated by a double-layer dipole a first magnetic image having an M×M resolution of data points; and the current dipole constructing system includes: a high resolution image synthesizer for receiving the first magnetic image and producing a higher resolution image representation of the first magnetic image by: accessing a linear model defining a model magnetic image of higher resolution than the first magnetic image, the linear model establishing interpolation patterns between characteristics of the linear model and the M×M data values of the first magnetic image; producing an intermediate magnetic image by projecting the first magnetic image onto the subspace of the linear model, and establishing coefficients for the intermediate magnetic image in accordance with the linear model and the M×M data values; submitting the intermediate magnetic image to an electric current localizer for determining the position and momentum of the electric current in accord with the intermediate magnetic image, the electric current localizer evaluating electromagnetic data in an x-y orientation (Bxy) assuming single dipole moment, computing dense Bxy from dense Bz, finding the image maximum in the intermediate magnetic image, and using this determined position information as a starting point in an iterative process for identifying a three-dimensional position vector $\vec{p}$ and momentum vector $\vec{J}$ for the electric current; and using the Biot-Sarvart Law for producing the higher resolution image representation of the first magnetic image based on the identified three-dimensional position vector $\vec{p}$ and momentum vector $\vec{J}$.

In this approach, the linear model is defined by creating a plurality of synthesized magnetic images having the same resolution as the second magnetic image, the synthesized magnetic images being based on simulated electrical impulses within a three-dimensional spatial conductive volume.

The electrical impulses may be double-layer dipoles and the synthesized magnetic images are based on randomly generated double-layer dipoles. The randomly generated double-layer dipoles have random depths, shapes and locations within the three-dimensional spatial conductive volume. Preferably, the linear model is created by using principal component analysis (PCA) and the three-dimensional spatial conductive volume is representative of cardiac tissue.

Alternatively, the synthesized magnetic images are based on randomly generated currents (single dipole moments) within the three-dimensional spatial conductive volume. Like before, the linear model is created by using principal component analysis (PCA) and the three-dimensional spatial conductive volume is representative of cardiac tissue.

Preferably, the interpolation patterns are established by the following steps: (A) defining the following notation: N×N dense Bz magnetic field map to form a vector; M×M sparse measurement to form a vector; K randomly generated single current dipoles Q; (B) for each randomly generated current Q, computing an N×N magnetic field map using Biot-Savart equation and stack the resultant image to a vector $f_1$; (C) repeating step (B) to obtain K samples and getting a data matrix $A=[f_1, f_2, \ldots f_K]$; and (D) training a PCA model given input data A, to obtain the eigenmatrix $\Sigma_f$.

In this approach, the intermediate magnetic image is created by: given a new dipole and M×M sparse measurements $g_j$, finding the corresponding rows in the eigenmatrix, and denoting a resultant submatrix as $\Sigma_g$; projecting the sparse measurement to the PCA subspace and computing the coefficients as $c_g = \Sigma_g^+ (g_j - g_{mean})$, where $\Sigma_g^+$ is the pseudo inverse of $\Sigma_g$; and using the computed coefficients and original PCA space to reconstruct the dense magnetic field map Bz, as $f_j = \Sigma f_{c_g} + f_{mean}$.

Also preferably, the producing of the intermediate magnetic image includes: defining the M×M data points as a vector g; defining the linear model as $\Sigma$; extracting from $\Sigma$ the row corresponding to each of the M×M data points to form a sub-eigenmatrix $\Sigma_g$; projecting g onto $\Sigma_g$; defining the establishment of coefficients as $c_g = E_g^+(g_t - \mu_g)$, where $\Sigma_g^+$ is the pseudo inverse of $\Sigma_g$, $\mu_g$ are extracted coefficients from a mean vector $\mu$ of linear model $\Sigma$; and defining the intermediate magnetic image vector h as $h = \Sigma \cdot c_g + \mu$.

Also in a preferred embodiment, identifying a three-dimensional position vector $\vec{p}$ and momentum vector $\vec{J}$ for the electric current may further include: given the intermediate magnetic image $B_z(i, j)(i=1, 2, \ldots, N; j=1, 2, \ldots, N)$, the maximal point of the tangential components $B'_{xy}(i, j)$ of $B_z(i, j)$ refers to the 2D position $(x_p, y_p)$ of the electric current, and the tangential components of $B_z(i,j)$ is computed as $B_{xy}(i,j) = \sqrt{(\partial B_z(i,j)/\partial x)^2 + (\partial B_z(i,j)/\partial y)^2}$; and the iterative process for identifying position vector $\vec{p}$ and momentum vector $\vec{J}$ for the electric current includes: (a) defining the Biot-Sarvart Law as $\vec{B}^m = \vec{J} \times \vec{R}_m = -\times \vec{J}$, where $\vec{B}^m = \vec{B}(\vec{r}_m)$, $\vec{J} = \vec{J}(\vec{p})$ and $$\vec{R}_m = \frac{\mu_0}{4\pi} \frac{(\vec{r}_m - \vec{p})}{\|\vec{r}_m - \vec{p}\|^3};$$

(b) expanding this definition of the Biot-Sarvart Law to a matrix form by using a skew-symmetric matrix:

$$\vec{B}^m = -[\vec{R}_m]_\times \vec{J}$$
$$= -\begin{bmatrix} 0 & -R_m^3 & R_m^2 \\ R_m^3 & 0 & -R_m^1 \\ -R_m^2 & R_m^1 & 0 \end{bmatrix} \cdot \begin{bmatrix} J^1 \\ J^2 \\ J^3 \end{bmatrix}$$

where the z component of the magnetic field is computed as:

$$B_z^m = [R_m^2, -R_m^1] \cdot [J^1, J^2]^T$$

where $R_m^1$, $R_m^2$ are x,y components of $\vec{R}_m$, and for the M×M data points one has a linear system:

$$\underbrace{\begin{bmatrix} B_z^1 \\ B_z^2 \\ \vdots \\ B_z^M \end{bmatrix}}_{B} = \underbrace{\begin{bmatrix} R_1^2 & -R_1^1 \\ R_2^2 & -R_2^1 \\ \vdots & \vdots \\ R_M^2 & -R_M^1 \end{bmatrix}}_{R} \cdot \underbrace{\begin{bmatrix} J^1 \\ J^2 \end{bmatrix}}_{J}$$

where B is a measured M×1 vector, R is a M×2 position matrix that is computed from given $\vec{p}$ and $\vec{\delta}_m$, and a lease square solution for J provides an estimateion of J defined as $J = (R^T R)^{-1} R^T B$;

(c) defining the Biot-Sarvart Law as $$\vec{B}^m = \frac{\mu_0}{4\pi} \frac{\vec{J} \times ((\vec{r}_o + \vec{\delta}_m) - \vec{p})}{\|(\vec{r}_o + \vec{\delta}_m) - \vec{p}\|^3} = \frac{\mu_0}{4\pi} \frac{\vec{J} \times (\vec{\varepsilon}_o + \vec{\delta}_m)}{\|\vec{\varepsilon}_o + \vec{\delta}_m\|^3}$$

letting $\alpha = 4\pi/\mu_0$ and $\vec{\varepsilon}_0 = \vec{r}_0 - \vec{p}$, identifying $\vec{\delta}_m$ as known for each data point to redefining the Biot-Sarvart Law as $$\alpha \vec{B}^m = \frac{\vec{J} \times \vec{\varepsilon}_o + \vec{J} \times \vec{\delta}_m}{\|\vec{\varepsilon}_o + \vec{\delta}_m\|^3}$$

letting $\vec{\tau}_m = \vec{J} \times \vec{\delta}_m$ and $\vec{\varepsilon}_0 = (x_\varepsilon, y_\varepsilon, z_\varepsilon)^T$ and computing $\vec{\tau}_m$ from $\vec{J}$, for each data point m=1:M, defining a nonlinear equation in terms of $(x_\varepsilon, y_\varepsilon, z_\varepsilon)$ as $$\alpha B_z^m + \frac{-J^2 x_\varepsilon + J^1 y_\varepsilon + \tau_m^3}{((x_\varepsilon + \delta_m^1)^2 + (y_\varepsilon + \delta_m^2)^2 + (z_\varepsilon + \delta_m^3)^2)^{3/2}} = f^m(x_\varepsilon, y_\varepsilon, z_\varepsilon) = 0$$

letting $F = (f^1; f^2; \ldots; f^M) = 0$, and solving a least square solution of the nonlinear system F for $\vec{\varepsilon}_0$; (d) using $\vec{\varepsilon}_0$ from step (c) to update the position matrix R and recompute J as in step (b), and iteratively repeating steps (b) and (c) until converges is achieved; and (e) defining the $\vec{p} = \vec{r}_0 - \vec{\varepsilon}_0$, and defining the initial depth z and magnitude $\|\vec{J}\|$ the electric current as $$z = d/\sqrt{2}.\ 3\ cm,\ \|\vec{J}\| = \frac{4\pi d^2 B_z^{max}}{0.385\ \mu_0}$$

where d is the distance between two magnetic poles in the third MCG image.

Other objects and attainments together with a fuller understanding of the invention will become apparent and appreciated by referring to the following description and claims taken in conjunction with the accompanying drawings.

BRIEF DESCRIPTION OF THE DRAWINGS

In the drawings wherein like reference symbols refer to like parts.

FIG. 17 tabulates the results of vertical double-layer dipole versus equivalent geometric center dipole moment comparisons.

FIG. 19 tabulates the results horizontal double-layer dipole versus equivalent geometric center dipole moment comparisons.

FIG. 20 tabulates the dipole localization error for vertical double-layer dipoles when comparing equivalent dipole moments calculated from MCG images with the true geometric center dipole moments.

FIG. 22 tabulates the dipole localization error for horizontal double-layer dipoles when comparing equivalent dipole moments calculated from MCG images with the true geometric center dipole moments.

FIGS. 26A to 26C show various equations (Eq. 1 to Eq. 14) to facilitate discussion of some aspects of the present invention.

versus depth, z.

Figure 29:
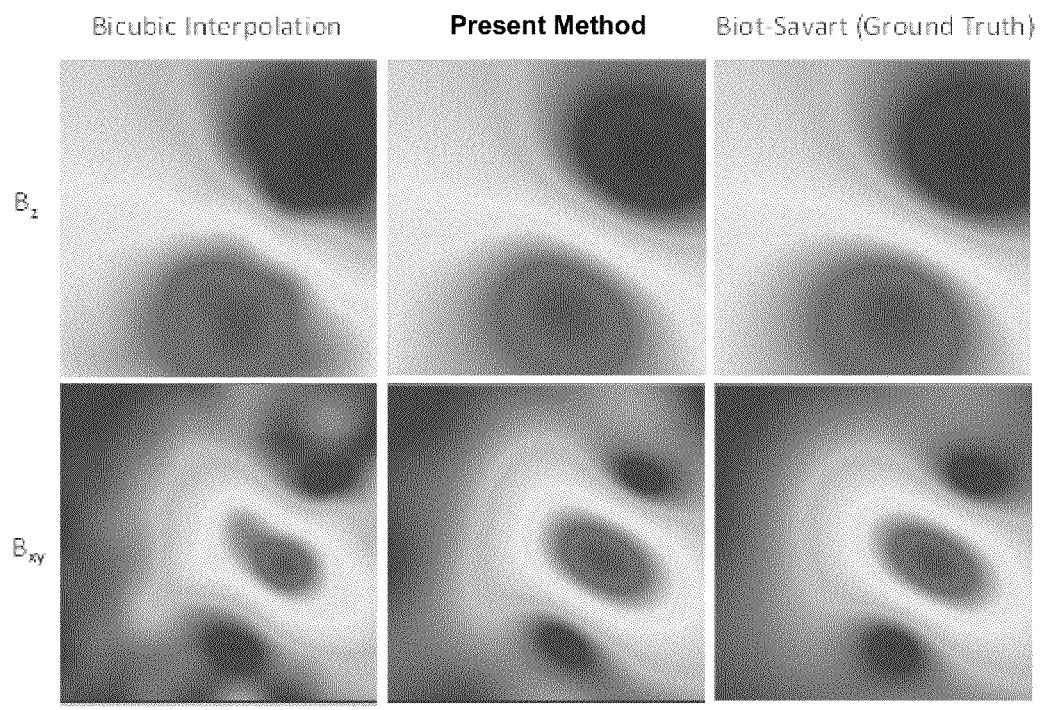

FIG. 29 compares high-res images generated by a presently preferred method and a prior art method with ground truth samples.

Figure 30:
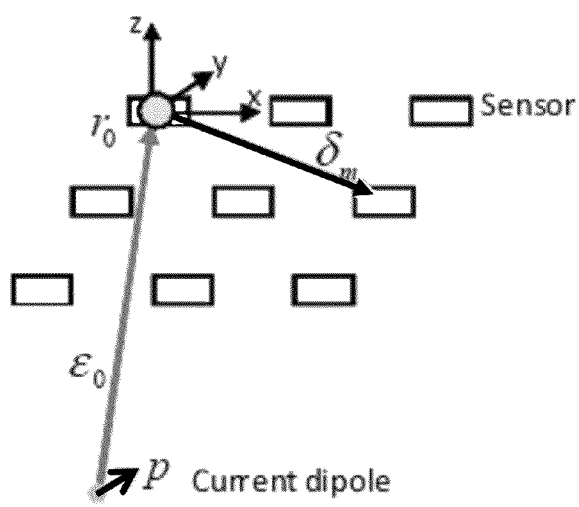

FIG. 30 illustrates a setup in the calculation of the inverse problem.

DESCRIPTION OF THE PREFERRED EMBODIMENTS

Electric current source estimation is a common problem in various electric imaging and magnetic imaging technologies. Estimation of a current source is beneficial in many research areas and clinical applications. For example, estimation of the position and moment of current sources in the brain has important implications for studying neuronal populations such as functional organization of cell assemblies, and localization of abnormal electric current sources in the heart is critical for diagnosing ischemic diseases such as myocardial infarction and angina cordis.

Figures 1A, 1B:
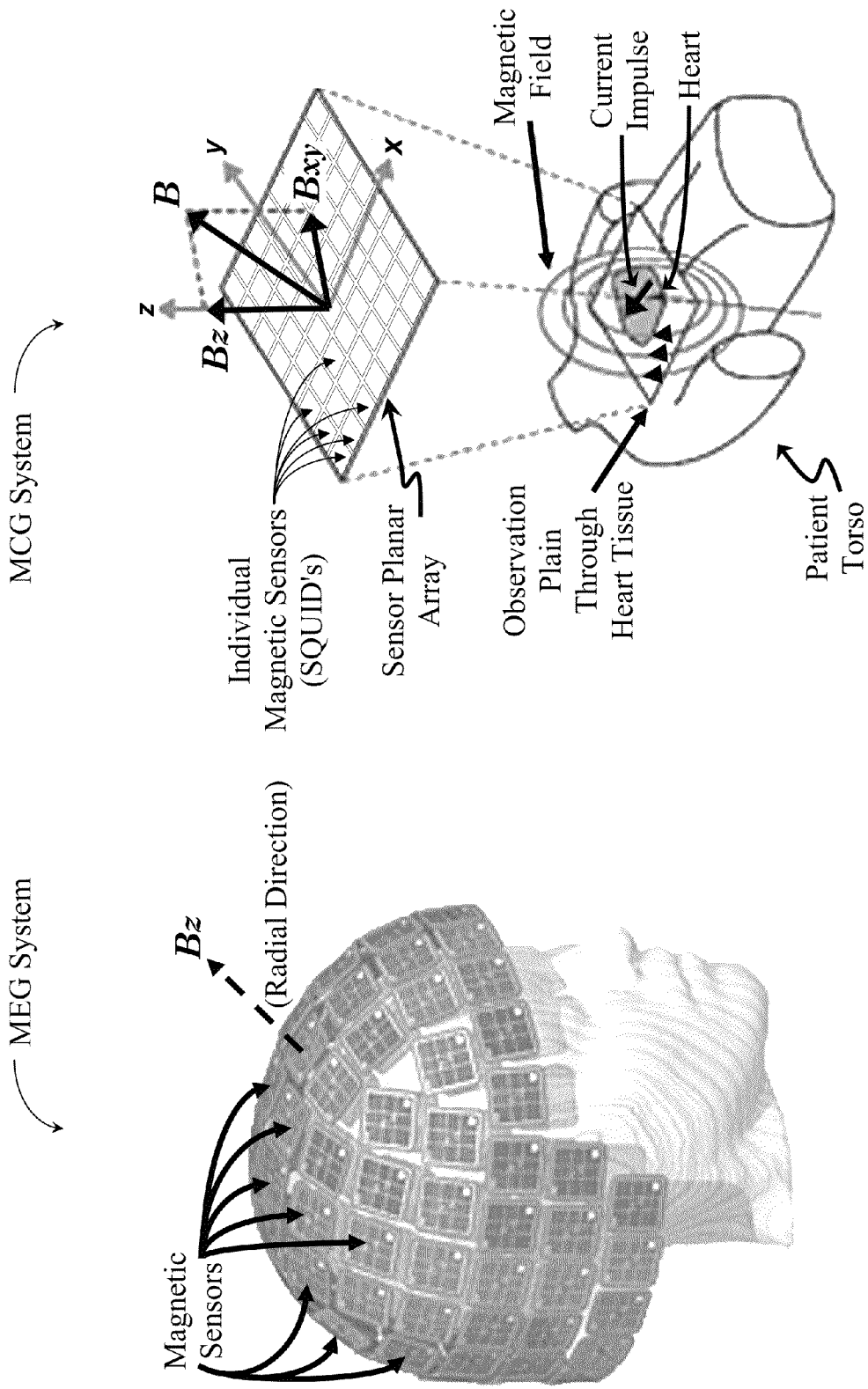
FIGS. 1A and 1B are examples of an MEG unit and an MCG unit, respectively.
Figure 2:
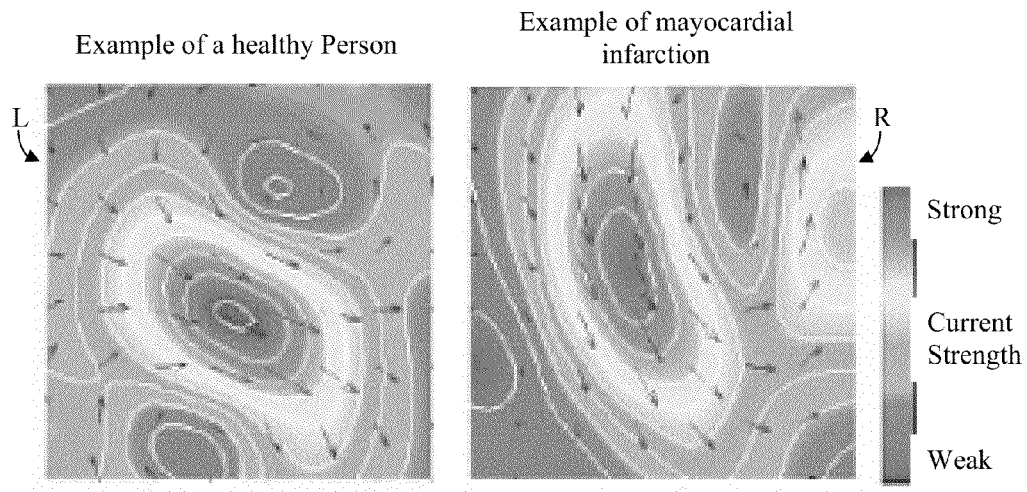
FIG. 2 shows two image examples of high-res 2D MCG images.
Figure 3:
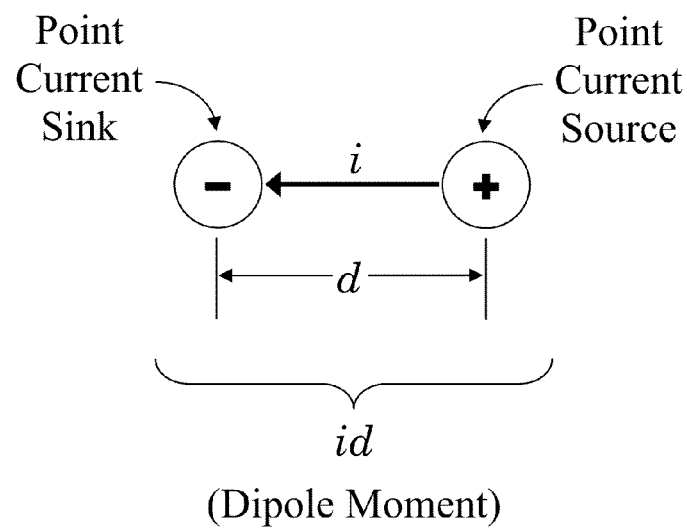
FIG. 3 illustrates a dipole moment.

The most basic electric current source within a tissue may be the current impulse (i.e. current dipole or dipole moment). FIG. 3 illustrates a point current source (the positive source) in close proximity to a point current sink (the negative source) of equal magnitude. If their strength is i and the distance between them is d, then they form a dipole moment id. However, nerve activity in tissue typically is the result of a plurality of such dipole moments acting together (and often acting in unison) across a surface of arbitrary shape and depth within a tissue.

Figure 4:
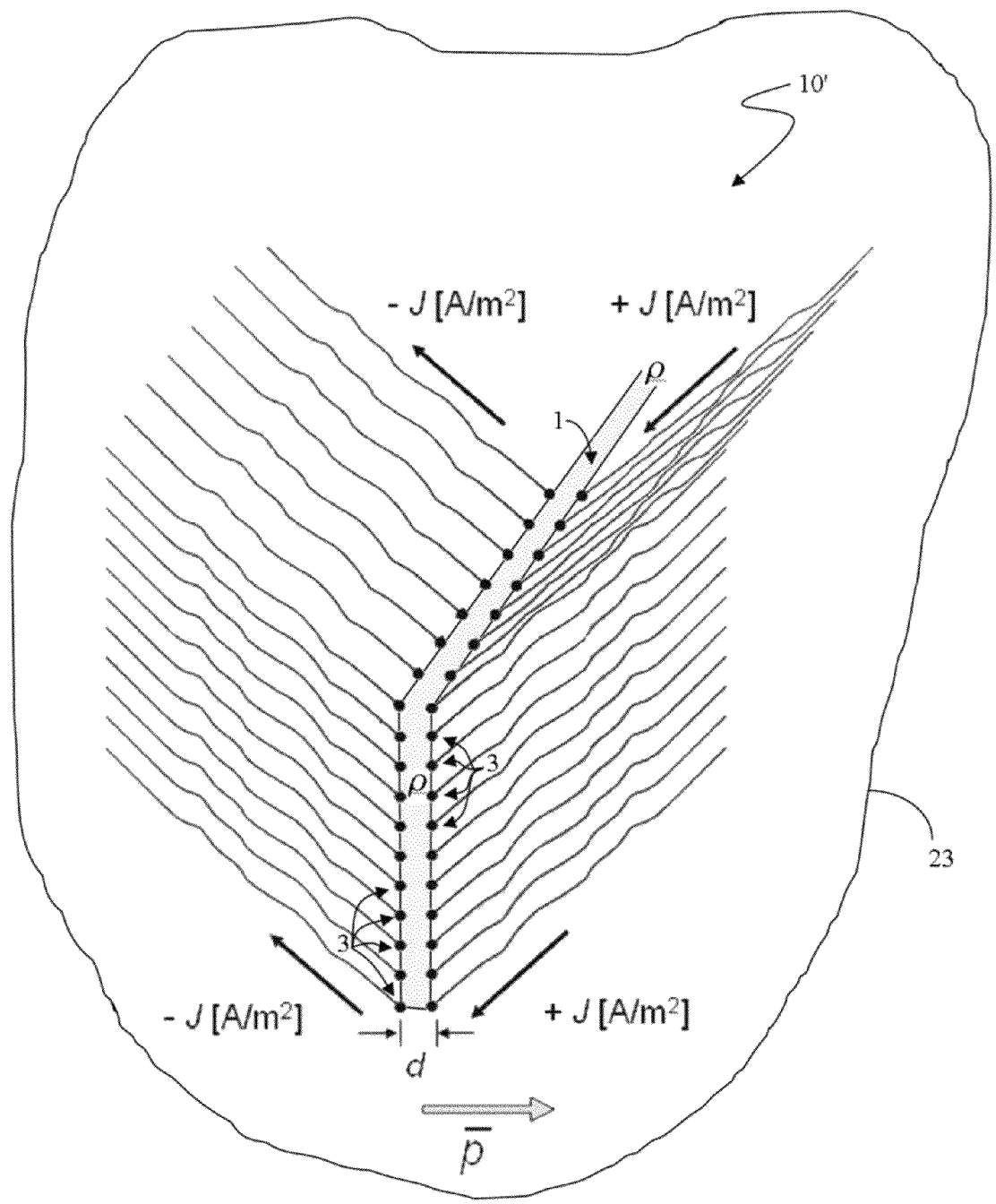
FIG. 4 illustrates a double-layer dipole.

A more appropriate view of the electrical activity in tissue is embodied by the double-layer dipole 10', as illustrated in FIG. 4. A smooth, conductive sheet (or layer) 1 of arbitrary shape, which defines two opposing surfaces, is illustrated lying within a volume conductor 23. Many dipole moments 3, as illustrated in FIG. 3, are uniformly distributed across sheet 1, with each point source and point sink pair being on opposite surfaces of sheet 1. In this manner, each dipole moment 3 is placed normal to sheet 1 and normal to its respective surface. It is assumed that the dipole density (i.e. density of dipole moments 3) is a well-behaved function of position, which means that the number of dipole moments 3 in a small area is great enough so that the density of dipole moments 3 can be well approximated with a continuous function. Such a source is termed a double-layer dipole 10'.

If the double-layer dipole 10' is denoted by $p(S)\bar{n}$, then $p(S)$ denotes a dipole moment density (dipole moment 3 per unit area) as a function of position, while its direction is denoted by $\bar{n}$, the surface normal. With this notation, $p(S)d\bar{S}$ is a dipole whose magnitude is $p(S)dS$, and its direction is normal to the surface at dS.

An alternate method of defining the double-layer dipole is to recognize that on one side of the double-layer dipole, the point current sources form a current density $+J[A/m^2]$ whereas on the other side the point current sinks form a current density $-J[A/m^2]$, and that the conducting sheet 1 (or layer) between the surfaces of the double-layer dipole has a resistivity $\rho$. The resistance across this sheet (of thickness d) for a unit cross-sectional area is $R=\rho d$, where R is the double-layer dipole resistance times unit area $[\Omega m^2]$, $\rho$ is the resistivity of the medium $[\Omega m]$, and d is the thickness of the double-layer dipole [m]. Since J is the double layer current density $[A/m^2]$, d is the double layer thickness [m], and p is the dipole moment per unit area [A/m], it is to be understood that the double-layer dipole arises only in the limit where $d \rightarrow 0$ while $J \rightarrow \infty$ such that $Jd \rightarrow p$ remains finite.

The following describes a method of generating double-layer dipole information from magnetic images. More specifically, an objective of the present invention is to locate double-layer dipoles using electromagnetic imaging. By way of example, the following discussion focuses on electromagnetic imaging of cardiac (i.e. heart) tissue, but it is to be understood that the following discussion is equally applicable to electromagnetic imaging in general, and in particular applicable to magnetic imaging of other types of tissues.

Fundamental to electromagnetic imaging of cardiac tissue (i.e. electrocardiography, ECG, and/or magnetoencephalography, MEG) is that the imaged cardiac tissue has a set of highly connected active cells that propagate with similar action potentials. It is further assumed that the cardiac tissue is homogeneous and isotropic, and thus all dipole moments (or dipole elements) lie in isochronal activation surfaces, and thus act in unison.

Figure 5:
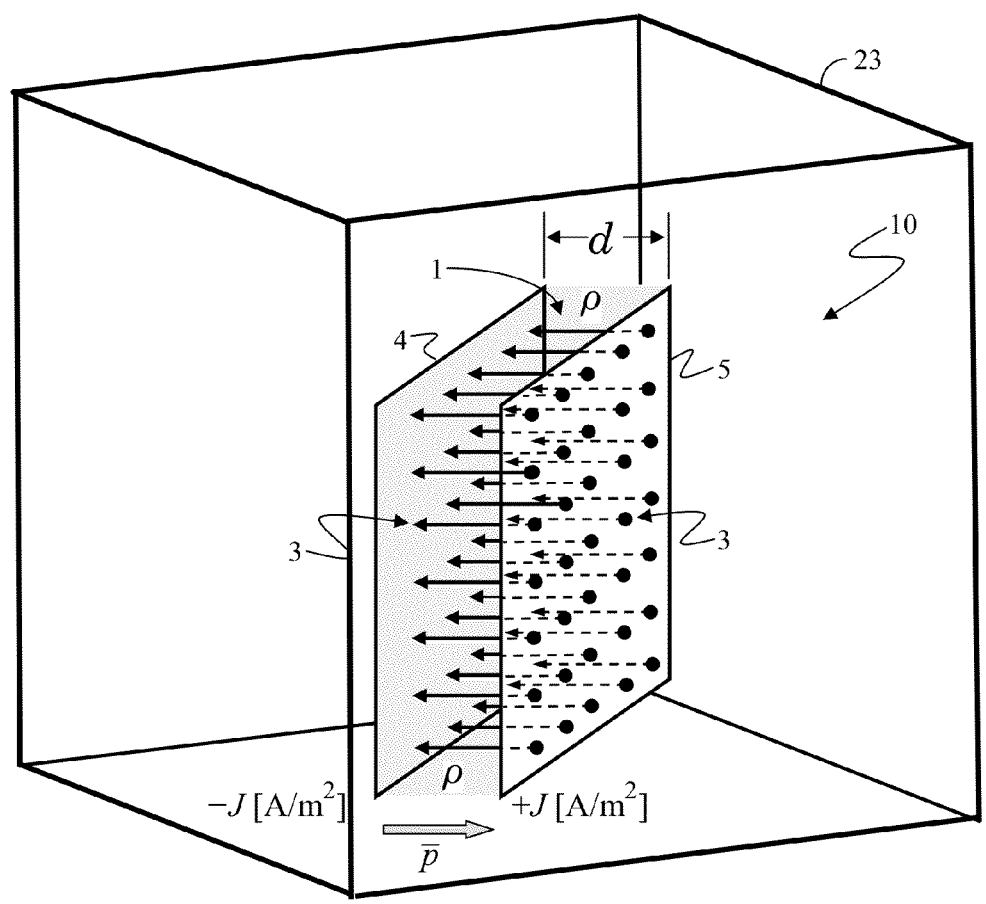
FIG. 5 is a simplified view of a double-layer dipole.

FIG. 5 illustrates a simplified double-layer dipole 10 for discussion purposes. All elements in FIG. 5 similar to those of FIG. 4 have similar reference characters and are described above. It is to be understood that the structure of simplified double-layer dipole 10 mirrors that of double-layer dipole 10'. The continuous dipole moments 3 of FIG. 4 are simplified in FIG. 5 as a set of multiple dipole moments 3 within volume conductor 23. In the present discussion, the opposing surfaces that define sheet 1 are each termed a double-layer 2D patch 4 and 5. Thus in the present construct, the double-layer dipole 10 is comprised of two opposing double-layer 2D patches 4 and 5, one corresponding to the set of point current sources (the positive sources), and the other corresponding to the set of point current sinks (the negative sources). In effect, double-layer 2D patches 4 and 5 divide double-layer dipole 10 into two parts; one part as seen from the positive side (double-layer 2D patch 5) and the other as seen from the negative side (double-layer 2D patch 4). Both sides produce a potential of equal magnitude, but opposite polarity.

At large distances from a double-layer dipole 10 or a dipole distribution such double-layer 2D patches 4 and 5 (i.e. at distances of multiple times the diameter of their surface), the observed electric field (and therefore the observed electric or magnetic, MCG, image) appears as if it originated from a single dipole moment whose strength and orientation are the vector sum of the source components (i.e. the individual dipole moments), as if they were all located at the same point. This single dipole moment may be termed an equivalent dipole moment of the double-layer dipole.

Figure 6:
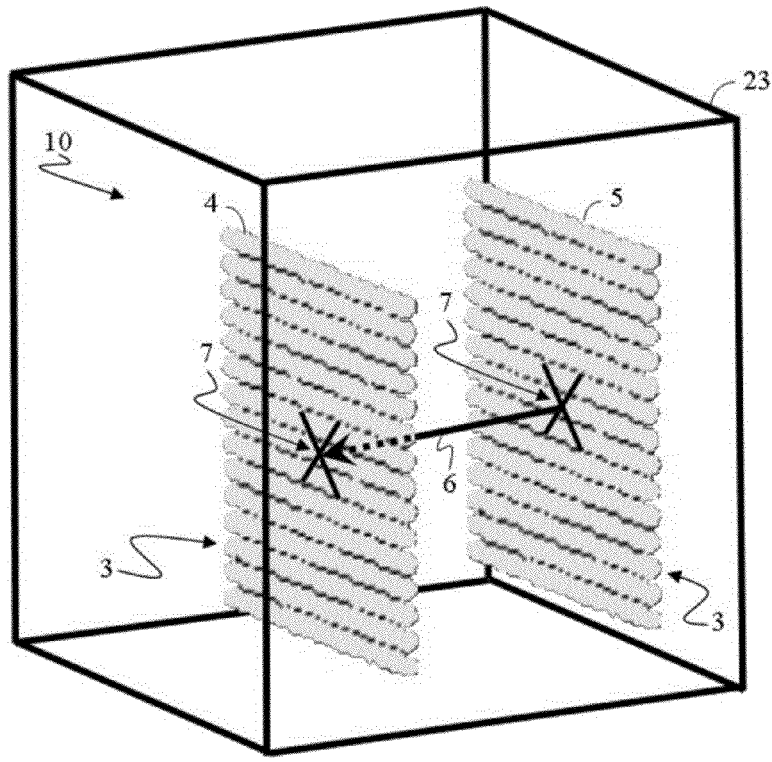
FIG. 6 is a second simplified view of a double-layer dipole highlighting two 2D patches and an equivalent dipole moment at their geometric center.

FIG. 6 illustrates a further simplification that combines the dipole distribution of double-layer 2D patches 4 and 5 into a single, equivalent dipole moment 6. As is explained above, a dipole moment equivalent to a double-layer dipole 10 may theoretically be identified by taking the vector sum of all the source components (i.e. the set of multiple dipole moments 3) within the double-layer dipole 10, and the resultant equivalent dipole moment 6 would make it appear as if all the source components were located at a common point. FIG. 6 addresses the question of how to determine the location of this common point. Rather taking the vector sum of all the source components, which is computationally impractical and physically infeasible due to there being no readily available method of physically identifying each individual source component, the presently preferred embodiment assigns the location of the equivalent dipole moment 6 to the geometric center of the double-layer dipole 10, which in FIG. 6 would correspond to the geometric center 7 of the double-layer 2D patches 4 and 5.

Having identified the location of equivalent dipole moment 6 as the geometric center of a double-layer 2D patch (4 or 5), determination of the magnitude and direction of equivalent dipole moment 6 makes use of additional simplifications. As is explained above, each of double-layer 2D patches 4 and 5 produce potentials of equal magnitude, and so FIG. 7 further simplifies the present problem by limiting itself to a single double-layer 2D patch 5. Because double-layer 2D patch 5 is only one side of a double-layer dipole 10, it may hereinafter bet termed a single double-layer dipole 5. Alternatively, since the present example illustrates a vertical single double-layer dipole, it may also be termed a vertical patch 5. In the present example, vertical patch 5 is constructed of 15×15 point sources, and thus it defines one layer of a double-layer dipole comprised of 15×15 dipole moments within conductive volume 23.

Figure 8:
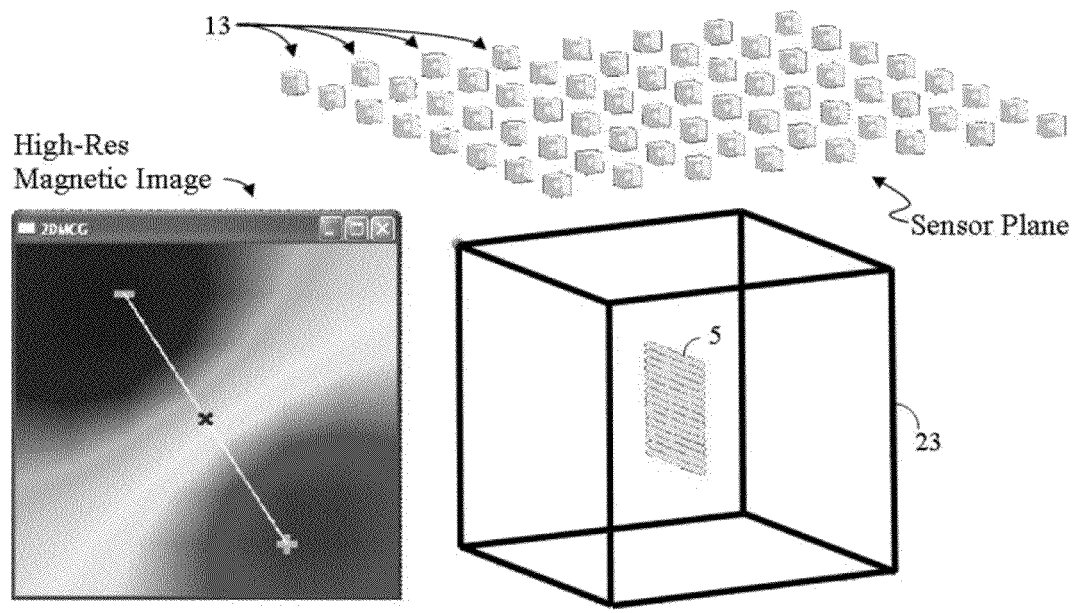
FIG. 8 illustrates vertical patch as observed by a sensor plane array of electromagnetic sensors.

FIG. 8 illustrates vertical patch 5 as observed by a sensor plane comprised of an 8×8 array of electromagnetic sensors 13. A high-res magnetic image of a magnetic field is also shown. Preferably, the propagation direction of observed double-layer dipoles (such as one represented by vertical patch 5) are defined to be parallel to sensor plane.

Figure 9:
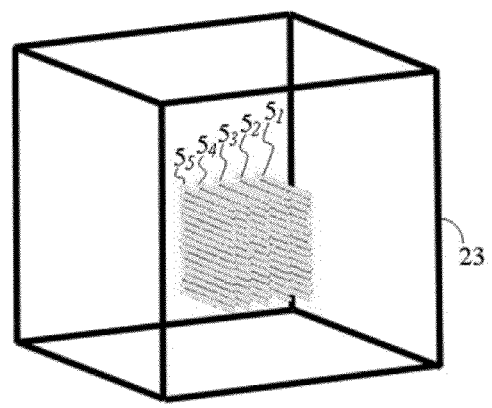
FIG. 9 illustrates five vertical patches within a conductive volume.

For illustration purposes, FIG. 9 illustrates five vertical patches, $5_1$ through $5_5$ within a conductive volume 23. This illustration of adjacent vertical patches is used to construct one definition of a horizontal patch in accord with the present invention.

Figure 10:
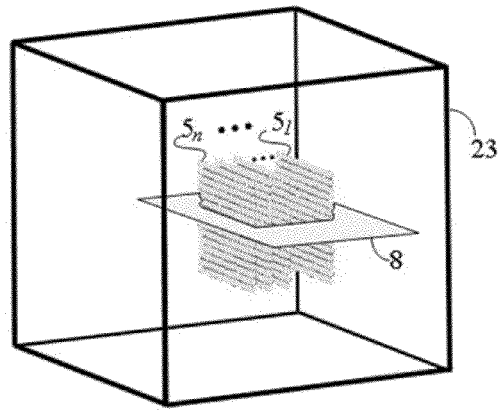
FIG. 10 illustrates a horizontal patch as a horizontal plane crossing multiple vertical patches.

With reference to FIG. 10, a horizontal patch, or layer, of point sources may preferably be defined in terms of a horizontal slice (or plane) 8 crossing multiple, adjacent, vertical patches, $5_1$ to $5_n$. In the present example, each of vertical patches $5_1$ to $5_n$ is defined by 15×15 point sources, and so plane 8 would define n individual (15×1) vertical patches, and the collection of these n adjacent (15×1) vertical patches would define one horizontal patch. That is, a horizontal patch may be defined as being comprised of a plurality of (X×1) adjacent vertical patches where each vertical patch is a 1D row, and X defines the number of point sources in a row.

Figure 11:
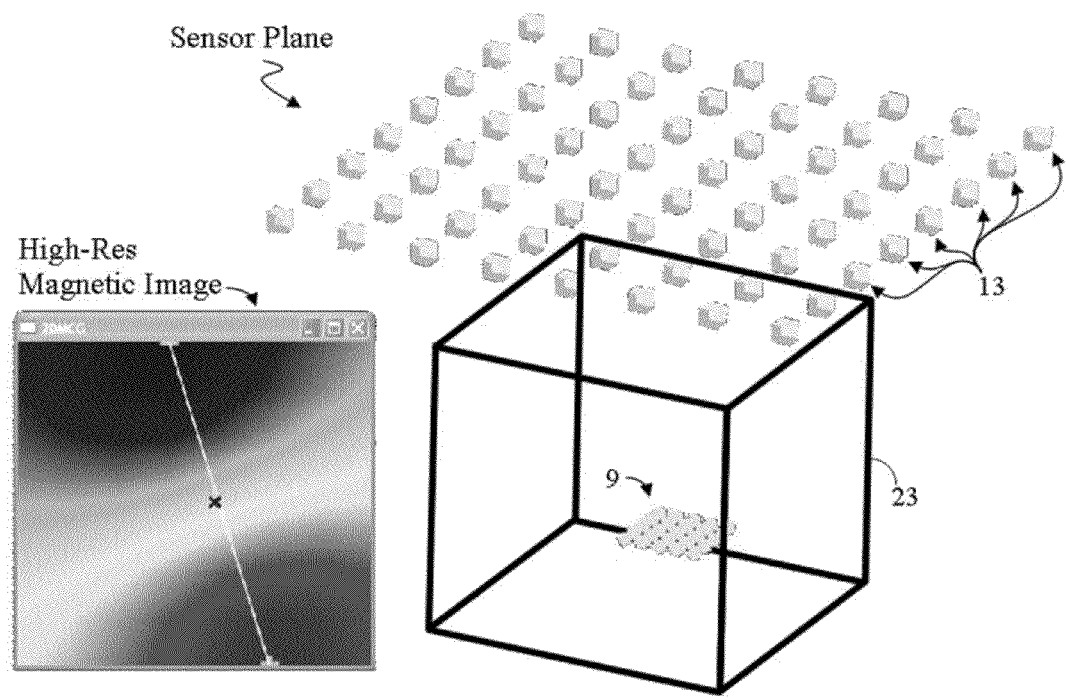
FIG. 11 illustrates a horizontal patch observed by a sensor plane of electromagnetic sensors.

FIG. 11 illustrates a 5×5 horizontal patch 9 observed by a sensor plane of 8×8 electromagnetic sensors 13. A high-res magnetic image of a magnetic field is also shown. As is explained above, a horizontal patch may be thought of as being comprised of multiple adjacent rows from adjacent vertical patches. Since each vertical patch is one side of a double-layer dipole, a horizontal patch may be defined as multiple zero depth, double-layer dipoles. Thus the propagation direction of double-layer dipoles defined by a horizontal patch may still be defined to be parallel to the sensor plane.

Figure 7:
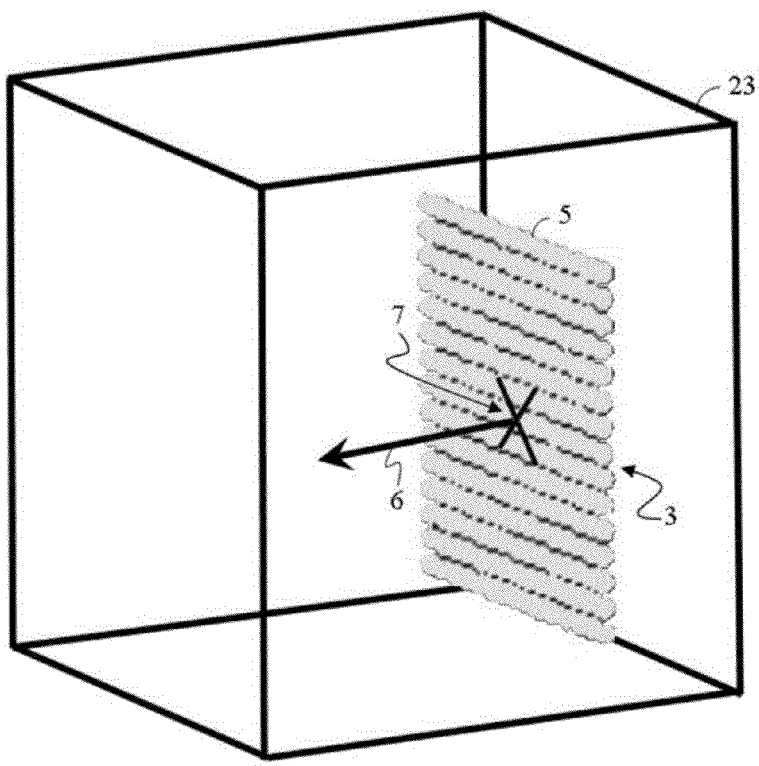
FIG. 7 illustrates a single double-layer 2D patch and it equivalent dipole moment at its geometric center.

A goal of the present invention is to locate double-layer dipoles from magnetic images. To achieve this, continuous dipole moments (see FIG. 4) are simplified to a set of multiple dipole moments, as illustrated in FIG. 5. Connected active cells (i.e. connected point sources) within a set of multiple dipole moments define a 2D patch. More specifically, a vertical patch (see FIG. 8) is defined by a single double-layer dipole, and a horizontal patch (see FIG. 11) is defined by multiple, zero depth, double-layer dipoles. The location of the double-layer dipole is defined as the geometric center 7 (see FIG. 6) of its corresponding single double-layer dipole (i.e. the geometric center of a corresponding vertical or horizontal patch), as illustrated in FIG. 7. Additionally, the propagation direction of a double-layer dipole is preferably defined in some embodiments to be parallel to a sensor plane.

The simplest double-layer dipole model has only one dipole moment, as illustrated in FIG. 3. A preferred method for locating and defining such as simple double-layer dipole within a captured magnetic image is explained below. But in order to locate and define a 2D patch, double-layer dipole comprised of a multiple dipole moments distributed over a plane, a first step is to compare the magnetic (i.e. magnetocardiography, or MCG) images generated from known double-layer dipoles and corresponding single dipole moments located at their geometric center. Next, the single dipole moment location method described below is applied to the MCG images of double-layer dipoles to locate corresponding equivalent dipole moments, each of which represents its corresponding double-layer dipole, in a magnetic sense (such as in terms of an equivalent magnetic field). Finally, the identified equivalent dipole moment is used to approximate the geometric center of the double-layer dipole, and the distance between the location of the identified equivalent dipole moment and the true geometric center of the double-layer dipole are compared.

With reference to FIGS. 12 to 15, before continuing with a discussion of the obtained results, it may be beneficial to first provide an overview of a preferred method of locating and defining an equivalent dipole moment from a given MCG image of a double-layer dipole. A more detailed description of the preferred method is provided further below.

Figure 12:
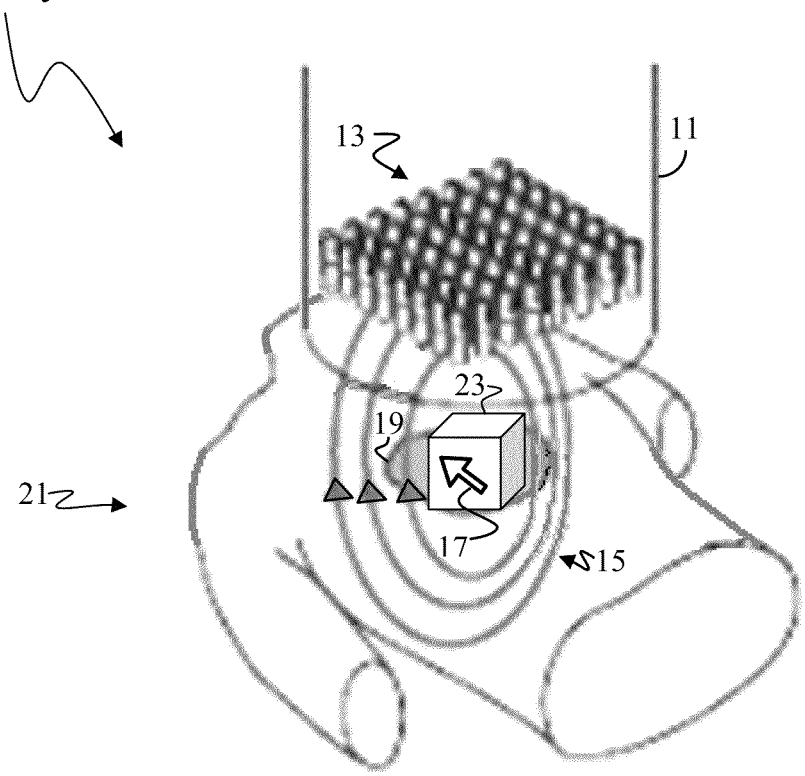
FIG. 12 illustrates an MCG system.

With reference to FIG. 12, a typical magnetocardiographic system consists of an MCG sensor unit 11 housing a small number of individual electromagnetic sensors 13, such as Superconducting Quantum Interference Device (SQUID) sensors. Electromagnetic sensors 13 are typically arranged as a planar array, and a typical magnetocardiographic system has sixty-four or fewer sensors. Electric impulses 17 within the body create a magnetic field 15. In the present case, the human heart 19 functions as the observed source of electric impulses 17 (i.e. as the current source).

Each electromagnetic sensor 13 is a capture point, and hereinafter may be referred to as a capture 13. Each capture 13 measures a one-dimensional (i.e. 1D) magnetic waveform in a direction perpendicular to the sensor planar array (i.e. the z-direction) emanating from the patient's chest 21 (i.e. human torso). By aligning (or synchronizing) the depth measures (i.e. the 1D magnetic waveform) of the array of captures 13 at a given depth in the z-direction, a two-dimensional (2D) MCG map (or MCG image) at the given depth may be constructed. The MCG sensor unit 11 is usually placed five to ten centimeters above the patient's chest 21, and measures the patient's heart magnetic field in a non-invasive manner. Thus, the array of captures 13 measure a collection of low resolution, two-dimensional (2D) MCG maps of electromagnetic activity.

In this manner, the magnetic sensors 13 continuously measure in the temporal domain the z-component of a magnetic field emanating from live tissue. This results in a series of 2D magnetic field images, where each 2D magnetic field image corresponds to a specific physiology time point, such as for example, the start of the atrial systole stage in the cardiac cycle. Using the obtained magnetic field measurements at different sites to attempt to estimate the location and moment of the current source that generated the observed magnetic field is called the inverse problem.

This estimated location and movement of the current source may be thought of as a current dipole (or flow dipole, or dipole moment) in 3D space. As it is known in the art, a flow dipole is a separation of a sink and a source. For example, applying this basic definition to a current dipole in a brain synapse (depending on whether the synapse is excitatory or inhibitory), the dendrite may serve as the source and the soma as the sink of the current dipole (or vise-versa).

Unfortunately, the images produced by magnetic sensors 13 do not provide sufficient resolution for meaningful interpretation. Therefore, an MCG system typically also requires a mechanism for converting low resolution MCG images to high resolution MCG images.

The presently preferred mechanism for converting low-res MCG images (i.e. low-res maps) to high-res images (i.e. high-res maps) makes use of a model of electrical activity for the given tissue, i.e. the human heart in the present case. Preferably, this model is a high-res model capable of receiving low-res, 2D MCG maps of electromagnetic activity, and outputting a simulated high-res, 2D MCG maps that correspond to the low-res, 2D maps. This may be achieved by simulating heart 19 as a block of heart tissue 23, and defining a high-res model based on the block of heart tissue 23.

The presently preferred mechanism for converting low-res MCG images (i.e. low-res maps) to high-res images (i.e. high-res maps) is based on a model learning algorithm, which is used to solve the inverse problem based on the set of sparse measurements provided by the magnetic sensors 13.

Figure 13:
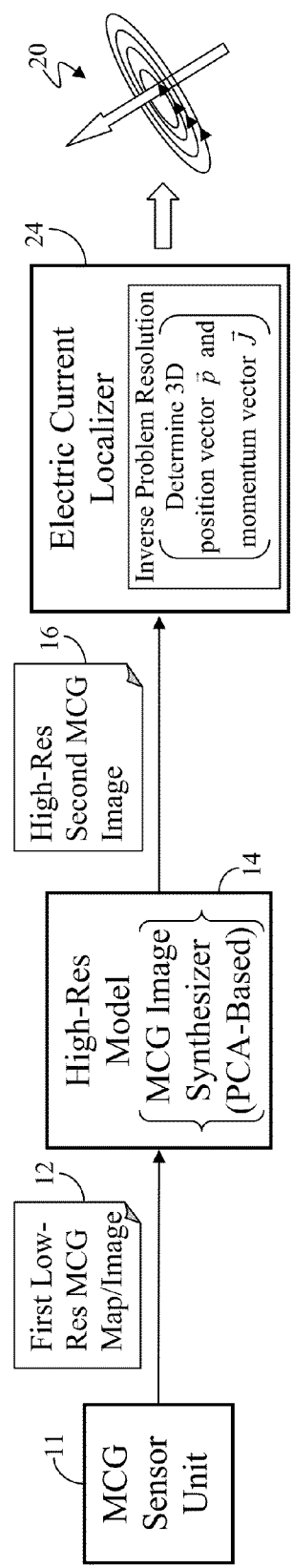
FIG. 13 illustrates a general flow of a simplified process in an MCG system that utilizes a high-res model.

A general process flow of a simplified process of this preferred mechanism is shown in FIG. 13. The physical MCG sensor unit 11 produces a first low-res MCG map (or image) 12, as explained above. This first low-res MCG image 12 is than passed to high-res model 14, which produces a high-res, 2D second MCG image 16.

Preferably, high-res model 14 is based on a principle component analysis (PCA) of a multitude of training high-res images, as is explained in more detail below. That is, high-res model 14 estimates the high-res 2D second MCG image by fitting a linear model with the sparse measurements obtained from the physical MCG sensor unit 11. The model may be constructed using a library of synthesized high-res training images, which may consists of a large number of randomly generated high-res magnetic field images based on the Biot-Savart law. High-res second MCG image 16 is a higher resolution image representation of first MCG image 12. For example, if first MCG image 12 has an M×M pixel resolution, then second MCG image 16 may have a P×P pixel resolution, where P>>M. Preferably, the high-res second MCG image has a resolution at least 20 times greater than the resolution of the low-res first MCG image. Further preferably, second MCG image 16 has a consistent, higher pixel density than first MCG image 12. For example, if first MCG image 12 spans an image area of 20 cm×20 cm, then its evenly distributed pixel density would be M×M pixels per 400 $cm^2$, whereas the evenly distributed pixel density for the corresponding, same image area of second MCG image 16 would be P×P pixels per 400 $cm^2$.

The high-res second MCG image 16 is submitted to electric current localizer 24, which resolves the inverse problem to estimate the three-dimensional (3D) location and moment of the current source 20 that generated the magnetic field depicted in the high-res second MCG image 16. That is, electric current localizer 24 determines the 3D position and momentum of an electric current in accord with the high-res second MCG image 16. Thus, estimated current source 20 corresponds to an equivalent dipole moment (or equivalent double-layer dipole).

Preferably, electric current localizer 24 evaluates electromagnetic output data as they would be observed in individual electromagnetic sensors in an x-y orientation (Bxy) assuming a single dipole and computes a dense Bxy from a dense Bz, where "B" refers to a magnetic field. Electric current localizer 24 then finds the image maximum in the intermediate MCG image 16, and uses this determined position information as a starting point in an iterative process for identifying a 3D position vector $\vec{p}$ and momentum vector $\vec{J}$ for the electric current.

The performance of high-res model 14 depends on the training images used to define it. For example in FIG. 14, a plurality of high-resolution, training images $42_a$ to $42_k$ are submitted to a principal component analysis (PCA) block 22 to define high-res model 14. At is point, the question is how to define the multitude of high-resolution training images $42_a$-$42_k$. As it would be understood, high resolution images/maps are not physically obtainable given the current state of the art of physical MCG sensor units, as depicted in FIG. 12. A presently preferred solution to this problem is to simulate the needed, high-resolution training images $42_a$ to $42_k$. In one embodiment, the simulated high-resolution training images $42_a$ to $42_k$ or of randomly generated double-layer dipoles. In an alternate embodiment, the simulated high-resolution training images $42_a$ to $42_k$ are of randomly generated single dipole moments.

Figure 14:
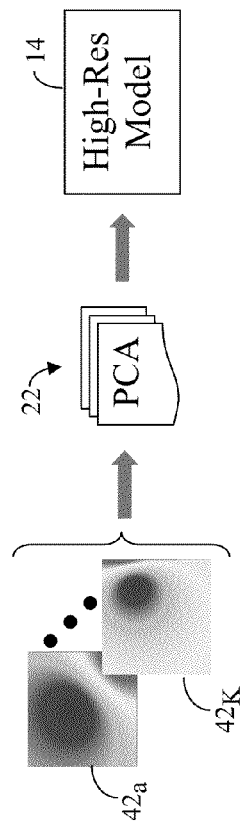
FIG. 14 shows a simplified summary of a preferred method of creating a high-res model by principal component analysis (PCA).
Figure 15:
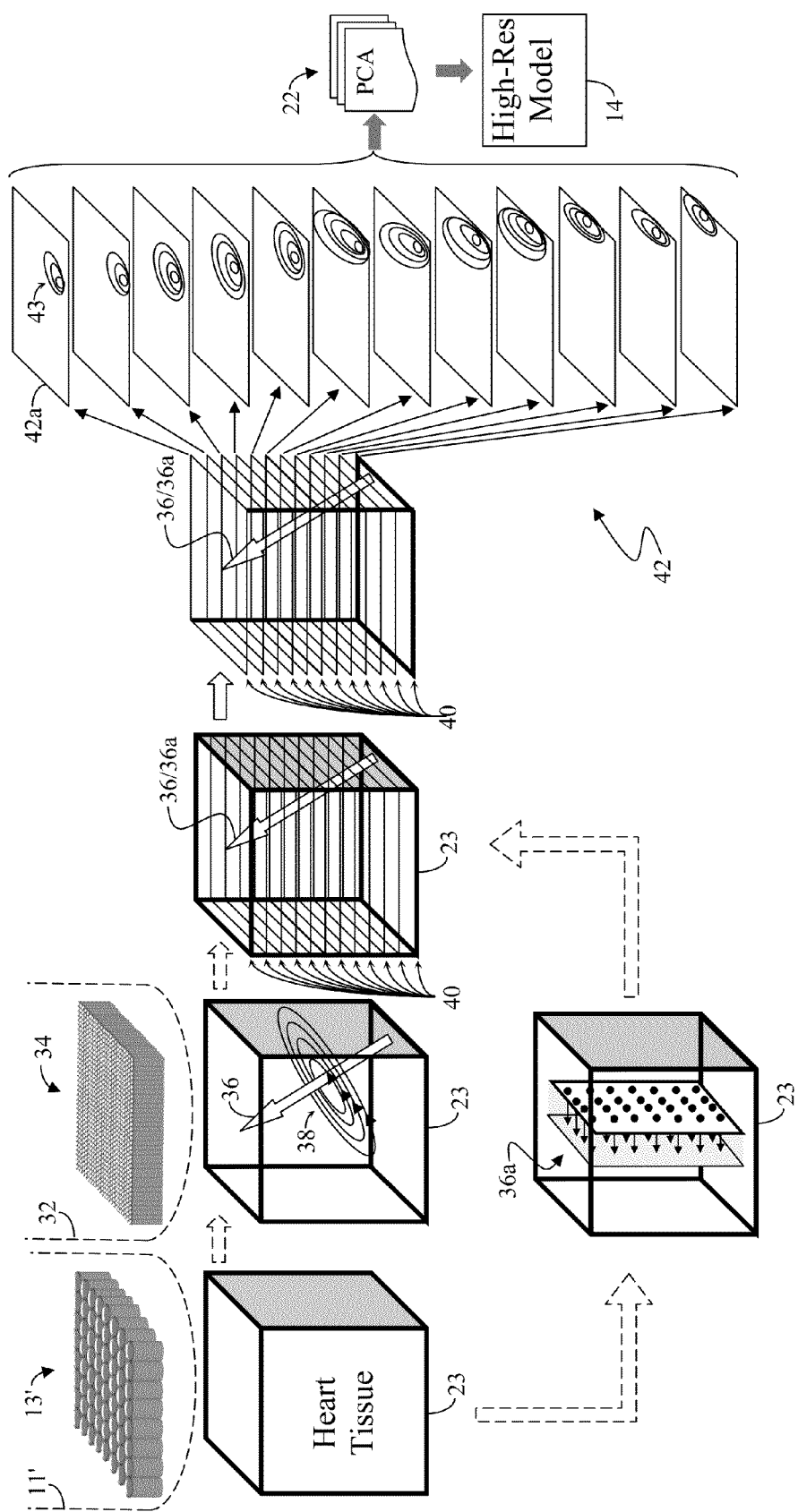
FIG. 15 is a more detailed summary of the method of FIG. 14.

With reference to FIG. 15, where all elements similar to those of FIGS. 12-14 have similar reference characters and are describe above, the basic ideal is to simulate heart 19 (shown in FIG. 12) as heart tissue block 23, and then to simulate a plurality of current impulses 36 (or double-layer dipoles 36a) within heart tissue block 23. Since the physical properties of heart tissue 23 (and any other intervening tissues/mediums between heart 19 and physical MCG sensor unit 11) are known, the propagation of a magnetic field through heart tissue block 23 as generated by current impulses 36 (or double-layer dipoles 36a) can be simulated. The size of heart tissue block 23 may be of comparable size as heart 19 (or of similar volume as an average human heart).

A simulated MCG sensor unit 11' similar to physical MCG sensor unit 11 of FIG. 12 is shown over heart tissue volume (i.e. block) 23. Simulated MCG sensor unit 11' could house a similar number of simulated electromagnetic sensors 13' as physical electromagnetic sensors 13 of FIG. 12. In this case, simulated MCG sensor unit 11' would be a low resolution MCG sensor unit, like that of FIG. 12. However, since an objective of the present case is to enhance the measurement readings from a physical MCG sensor unit, and since one is free to define simulated MCG sensor unit 13' to have any desired features, it is preferred that low resolution simulated MCG sensor unit 11' be replaced with a hypothetical, high resolution, simulated MCG sensor unit 32.

Hypothetical high-res MCG sensor unit 32 would have a similar resolution as the desired high-res training MCG images $42_a$-$42_k$, and thus would house a larger array 34 of simulated electromagnetic sensors, one per pixel of a desired high-res MCG image. Random, current impulse 36 (or random double-layer dipoles 36a) could now be defined within heart tissue volume 23, and its resultant magnetic field 38 generated by use of the Biot-Savart Law. High-res MCG sensor unit 32 would now make high resolution readings (i.e. generate high-res, training MCG images) of the magnetic field 38 at various depths within heart tissue volume 23.

For practical reasons, it is preferred to generate high-res training MCG images at a predefined, limited number of depths, or layers 40 within heart tissue volume 23. The individual layers 40 can then be extracted from heart tissue volume 23, and separated to create individual high-res training MCG images 42 for each depth level. It is to be understood that a multitude of random current impulses (or random double-layer dipoles) would be defined, their magnetic fields generated, and resultant level images created. In one embodiment, 1000 random current impulses (or random double-layer dipoles) are defined, and 1000 sample images are created per depth level. These simulated high-res, training MCG images 42 are then used to construct PCA-based, high-res MCG image model 14.

Returning now to a discussion of experimental results obtained in the preferred embodiment. The experiment had the following makeup:
8×8 sensors, with 2.5 cm spacing between sensors
5% uniformly distributed noise
Unknown depth
Unknown orientation
Double layer dipole patches defined as:
A) Vertical patch:
i) x=1, 3, . . . , 15, z=1, 3, . . . , 15
ii) 0.25 cm spacing
iii) 150 trials
iv) Random position B) Horizontal patch
i) x=1, 3, . . . , 21, z=1, 3, . . . , 21
ii) 0.25 cm spacing
iii) 200 trials
iv) Random position A first step is to compare MCG images generated from double layer dipoles with an single, equivalent dipole moment at their geometric center. As is explained above, this may be done using 2D patch, double-layer dipoles. Vertical patches (i.e. vertical double-layer dipoles) of various sizes are compared first, followed by comparison of horizontal patches (i.e. horizontal double-layer dipoles). As shown in the experimental set-up immediately above, 150 trials at random positions are run for each double-layer size. Their maximum and minimum errors are then determined.

Figure 16:
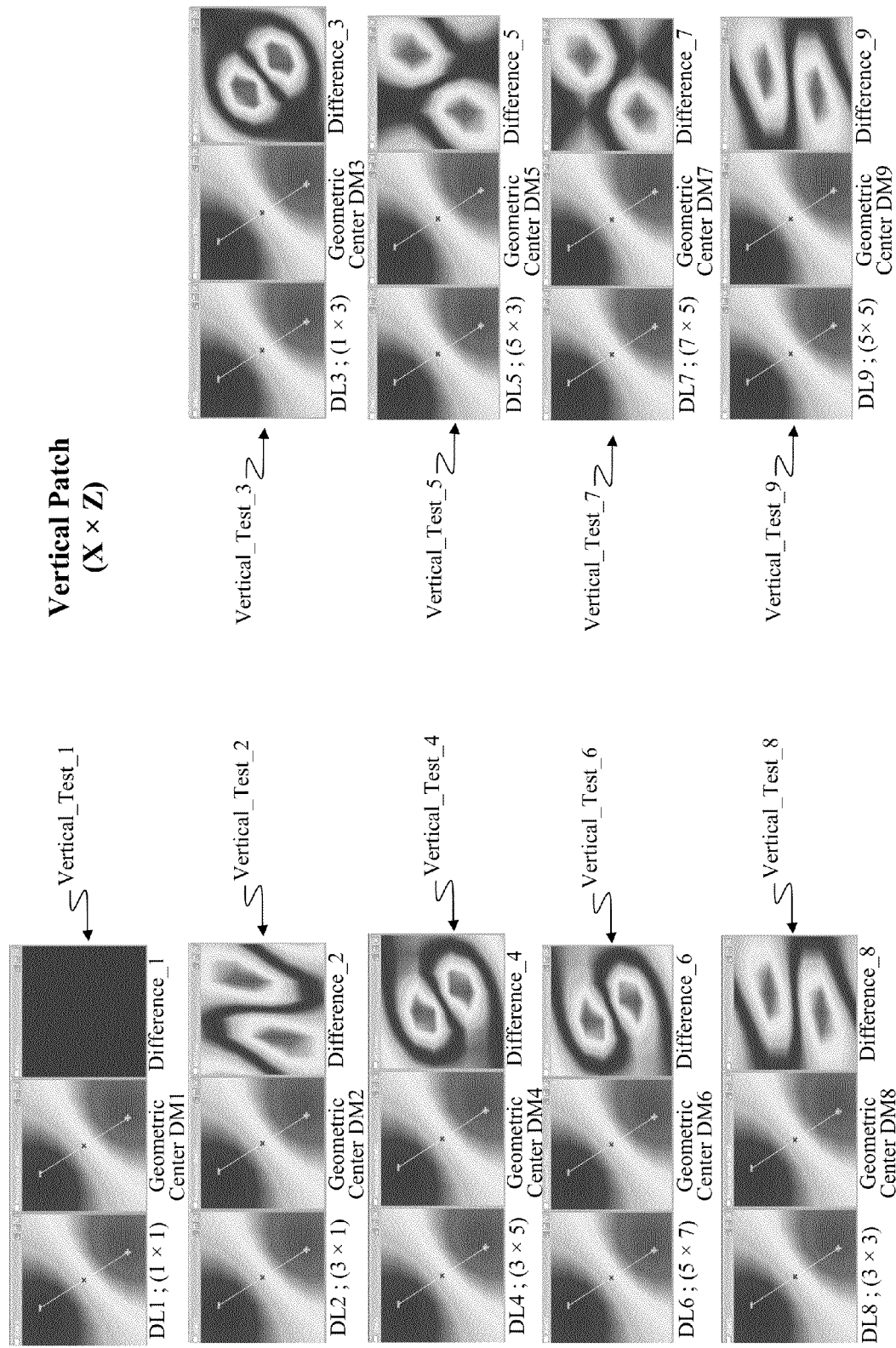
FIG. 16 illustrates a comparison of nine vertical double-layer dipoles of various sizes with their corresponding single dipole moments at their respective geometric centers.

FIG. 16 illustrates nine tests (vertical_test_1 through vertical_test_9), where the tests compare vertical double-layer dipoles (DL1 through DL9) of various sizes with their corresponding single dipole moments at their respective geometric centers (geometric center DM1 through DM9). The difference between the two (i.e. their comparison results) are shown as difference_1 through Difference_9. Double-layer dipoles DL1 to DL9 are MCG images generated from double-layered sources (normalized by local a maximum/minimum reference). The geometric center dipole moments (DM1 to DM9) may be viewed as MCG images from an averaged source (normalized by local maximum/minimum). Difference_1 to difference_9 are the MCG error images (normalized by local maximum and minimum).

The sizes of vertical double-layer dipoles are illustrated as (X×Z) to specify their width by their height. The size of DL1 is (1×1), which is the same as a single dipole moment. Therefore, MCG error image difference_1 shows no difference between DL1 and DM1. Differences are apparent, however, in vertical_test_2 through vertical_test_9. As is evident from difference_2 through difference_9, the distribution of MCG image differences is center symmetric.

The results of these vertical double-layer dipole versus equivalent geometric center dipole moment comparisons are tabulated in FIG. 17. As shown, The larger sizes of double-layer dipole sources correspond to larger MCG error images difference. Nonetheless, even the maximum error (i.e. the difference between MCG images) is small, and so using the equivalent dipole moment to approximate the geometric center of the double-layer dipole is a valid solution.

Figure 18:
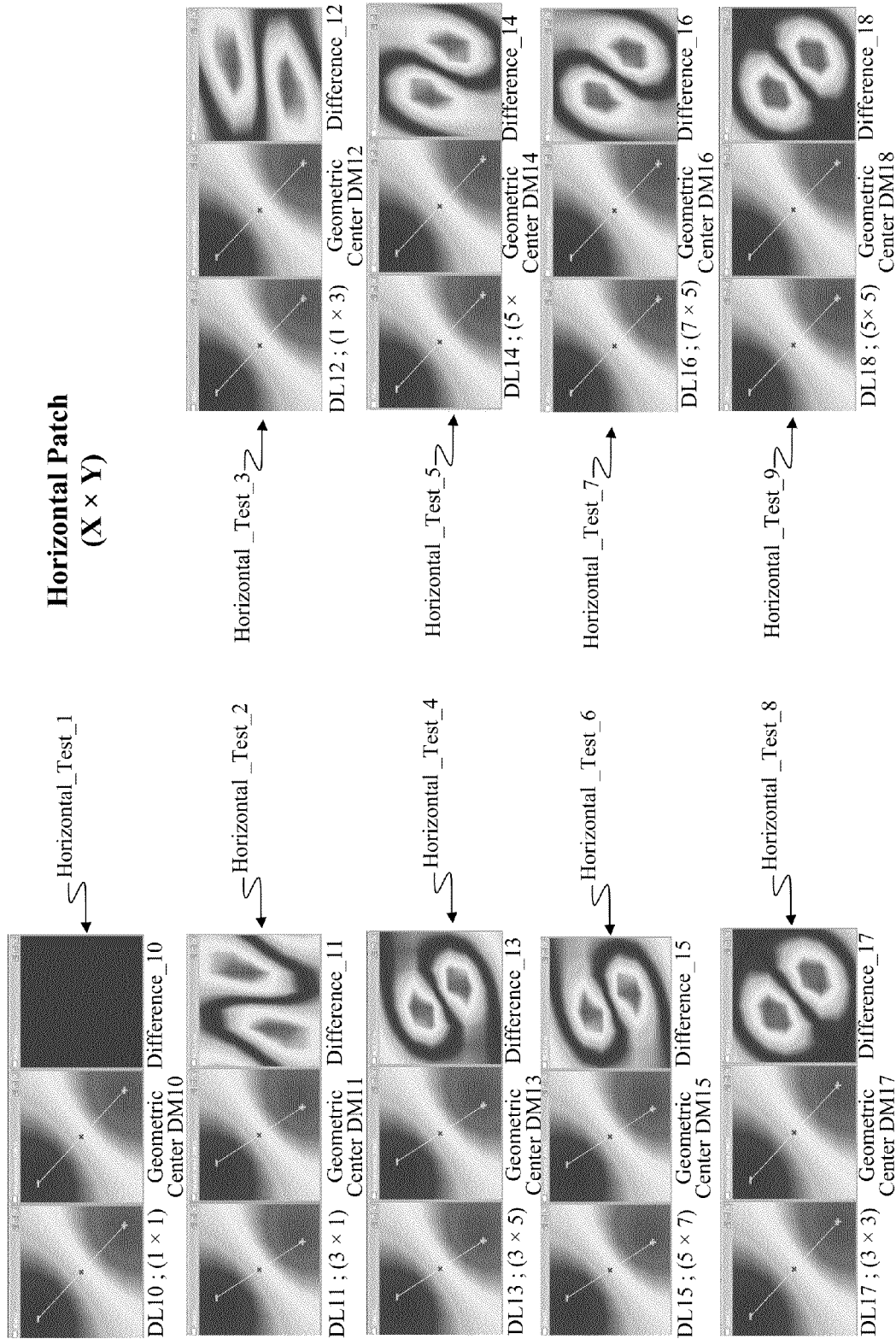
FIG. 18 illustrates the comparison of nine horizontal double-layer dipoles of various sizes with their corresponding single dipole moments at their respective geometric centers.

FIG. 18 illustrates the comparison of nine tests (horizontal_test_1 through horizontal_test_9) of nine horizontal double-layer dipoles (DL10 through DL18) of various sizes with their corresponding single dipole moment at their geometric center (geometric center DM10 through DM18). The difference between the two (i.e. their comparison results) are shown as difference_10 through Difference_18. Double-layer dipoles DL10 to DL18 are MCG images generated from double-layered sources (normalized by local a maximum/minimum reference). The geometric center dipole moments (DM10 to DM18) may be viewed as MCG images from an averaged source (normalized by local maximum/minimum). Difference_10 to difference_18 are the MCG error images (normalized by local maximum and minimum).

The sizes of horizontal double-layer dipoles are illustrated as (X×Y) to specify their width by their length. The size of DL10 is (1×1), which is the same as a single dipole moment. Therefore, MCG error image difference_10 shows no difference between DL10 and DM10. Differences are apparent, however, in horizontal_test_2 through horizontal_test_9. As is evident from difference_11 through difference_18, the distribution of MCG image differences is again center symmetric.

The results of these horizontal double-layer dipole versus equivalent geometric center dipole moment comparisons are tabulated in FIG. 19. As in the case of vertical double-layer dipoles, the larger sizes of horizontal double-layer dipole sources correspond to larger MCG error images difference. But like before, even the maximum error is still relatively small, and so using the equivalent dipole moment to approximate the geometric center of the double-layer dipole is a valid solution for horizontal double-layer dipoles, as well.

Now that its been established that the use of the geometric center of a double-layer dipole is valid for determining the location of dipole moment equivalent to (i.e. represents) a double-layer dipole (at least at some distance from the double-layer dipole), the next question to be addressed is how to best identify the equivalent deponent moment given an MCG image of a double-layer dipole. The General process shown above in reference to FIGS. 12-15 (a more detailed description of this process is provided below) was used to calculate an equivalent dipole moment. The results were then compared with the true geometric center equivalent to determine the error.

This dipole localization error is tabulated in FIGS. 20 and 22, which compares the calculated, equivalent dipole moments to the true geometric center dipole moments. FIG. 20 tabulates the error for vertical double-layer dipoles and FIG. 22 tabulates the error for horizontal double-layer dipoles.

Figure 21:
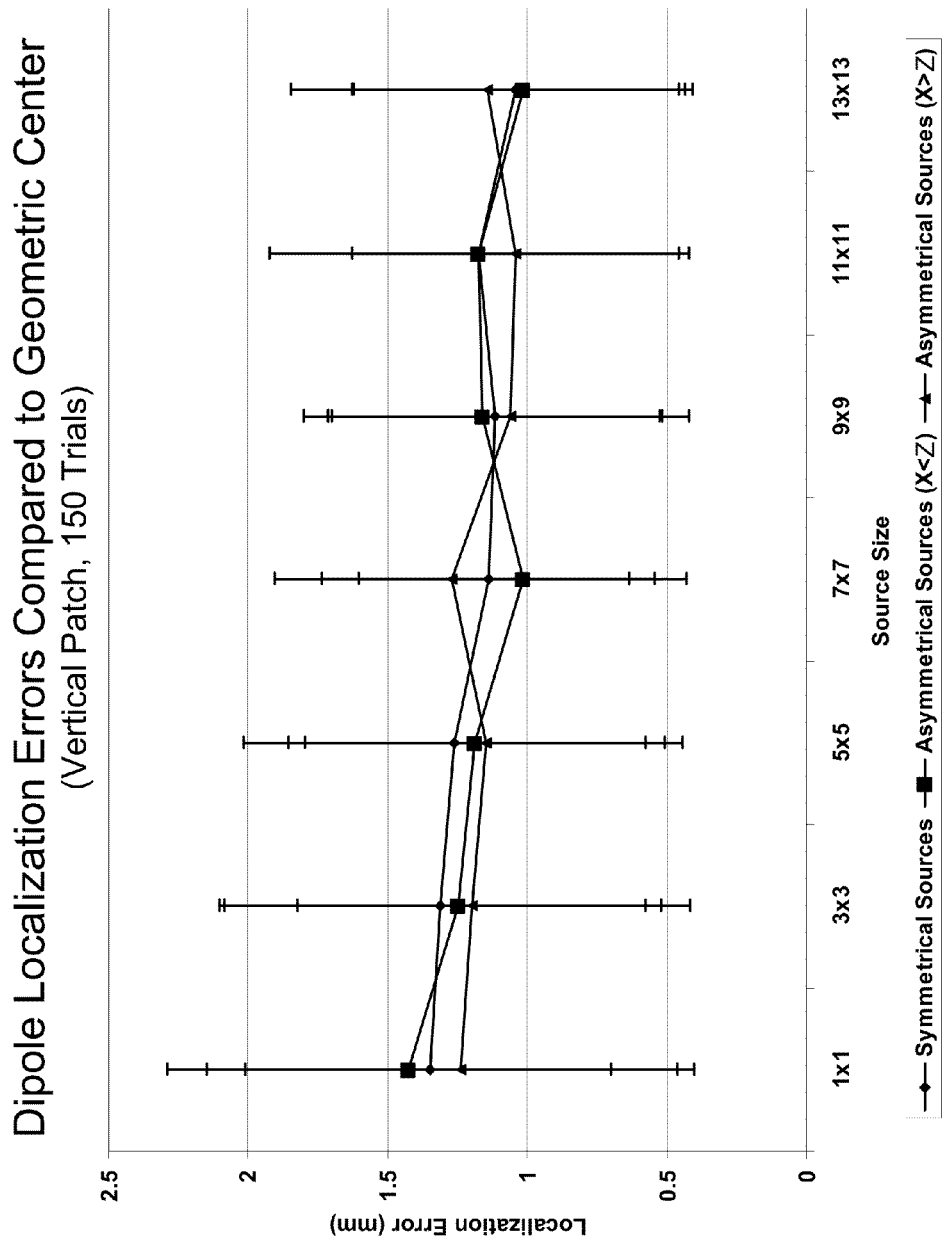
FIG. 21 shows a chart of the dipole moment location errors for vertical double-layer dipoles in over 150 trials.

For ease of illustration, FIG. 21 shows a chart of the dipole moment location errors for vertical double-layer dipoles for 150 trials. The amount of error is affected by whether the double-layer dipole is symmetrical, asymmetrical with X<Z, or asymmetrical with X>Z.

Figure 23:
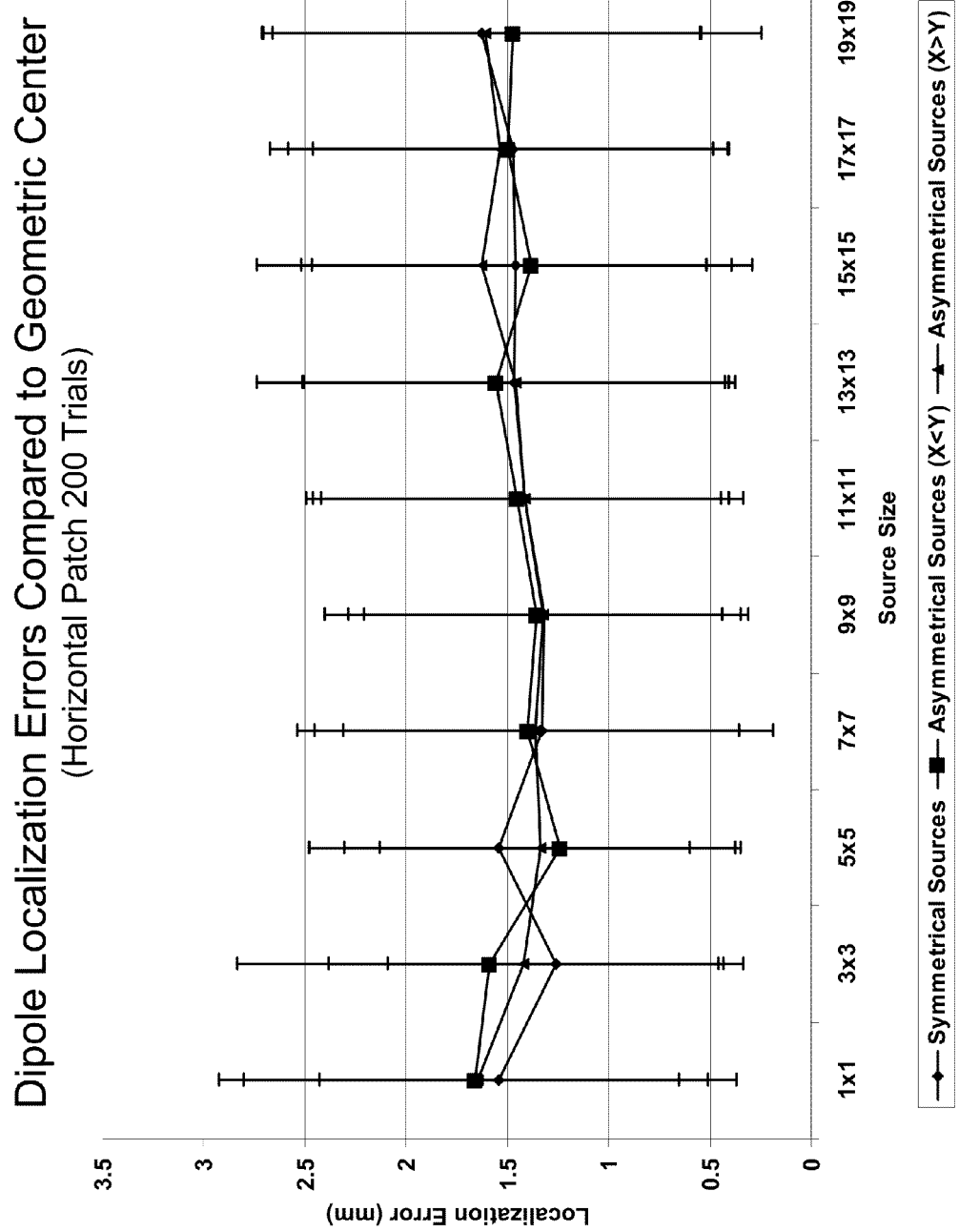
FIG. 23 shows a chart of the dipole moment location errors for horizontal double-layer dipoles in over 200 trials.

Similarly, FIG. 23 shows a chart of the dipole moment location errors for horizontal double-layer dipoles for 200 trials. Again, the amount error is affected by whether the double-layer dipole is symmetrical, asymmetrical with X<Y, or asymmetrical with X>Y.

From FIGS. 20-23, it is evident that the average accuracy of symmetrical sources is a little bit better than the average accuracy of asymmetrical sources. Additionally, when the source size is about the same size of the sensor spacing (e.g. 10×10 sources=2.5 cm×2.5 cm), the localization error is a bit smaller. But overall, the calculated equivalent dipole moment is very close to the geometric center. Therefore, the calculated, equivalent dipole moment can be validly used to approximate the geometric center of a double-layer dipole. Furthermore, the same accuracy can be achieved using the present method as the method of locating the single dipole model using the more rigorous averaging method, which requires knowledge of each of the dipole moments distributed across a double-layer layer. This accuracy is achieved no matter the size and/or asymmetrical distribution of sources.

For more complicated double-layer dipoles, a model based on 3D voxels may be appropriate. Additionally, accuracy may be improved by building a regression model.

A more detailed description of a preferred method for calculating the equivalent dipole moment from a given MCG image now follows.

Thus, the present embodiment utilizes various computing devices (or data processing devices) to learn (i.e. create) a linear model from a set of synthesized high-res MCG images generated by random electric impulse currents (or random double-layer dipoles). Sparse data (i.e. a low resolution image) received from a physical/real MCG sensor unit is then projected onto the linear model, and a high resolution image representation of the low resolution image is created there from.

Figure 24:
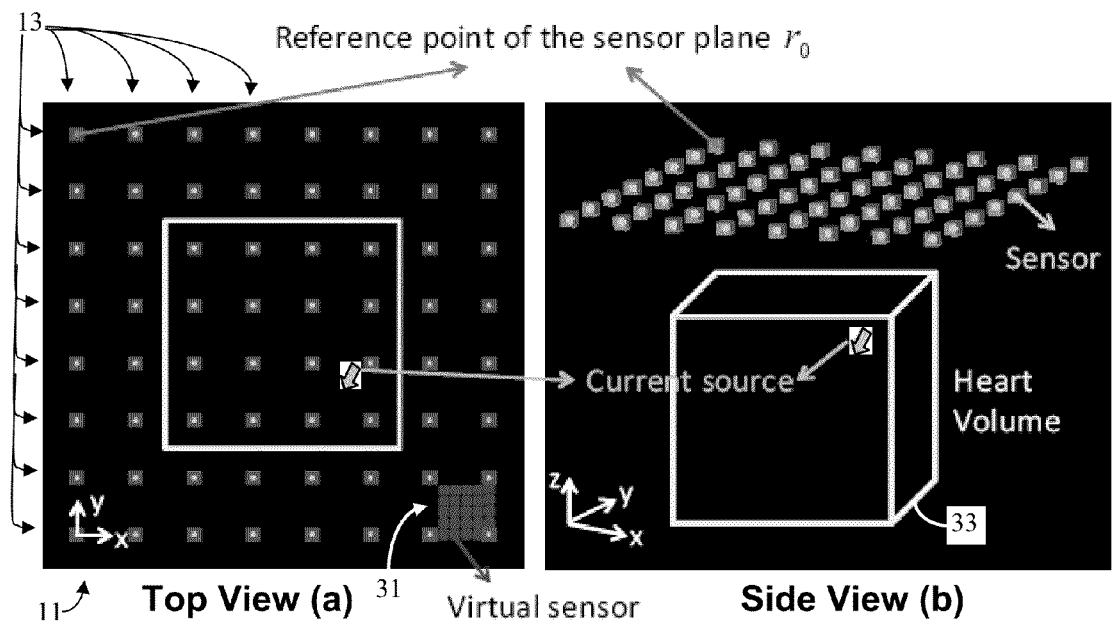
FIG. 24 illustrates the top view and side view of a 3D spatial heart volume in a simulation setup.

With reference to FIG. 24, Top View (a) illustrates a top-view of a 2D sensor array (or sensor plane) in relationship to a side-view, 3D spatial heart volume 33 [Side View (b)] in a simulation setup. In the present example, Top View (a) illustrates a top view of an MCG sensor unit (such as MCG sensor unit 11 of FIG. 12) with 64 physical sensors 13 (such as electromagnetic (SQUID) sensors 13) arranged in an 8×8 sensor array. In the present embodiment, however, a set of four virtual sensors 31 are inserted in-line between adjacent real, physical sensors 13 in the x- and y-directions. Additionally, the square area defined by four corner physical sensors 13 and their four aligned sets of virtual sensors 31 is filled with a 4×4 array of additional virtual sensors 31. Thus, the present embodiment adds 1232 virtual sensors 31 to the 64 physical sensors 13 for a total of 1296 simulated sensors. This is equivalent to a 36×36 sensor array, and constitutes the basis for one implementation of the present, simulated, high-res, training images. Assigning one image pixel per sensor, the present implementation thus provides for P×P (P>8) pixels in a high-res MCG image. Preferably, the sensor plane is 5 cm to 10 cm above heart volume bounding box 33, which in the present case is 10 cm³ (i.e. 10 cm×10 cm×10 cm). In this example, the pixel density in each high-res MCG image would be (1296 pixels)/(100 cm²), or about 13 pixels per square centimeter (i.e. the high-res image has more than 20 times the resolution of the low-res image). The electric current is represented by a vector located at a 3D point.

It is to be understood that the number of virtual sensors, and thus the value of P is a design choice. FIGS. 26A to 26C show various equations (Eq. 1 to Eq. 14) to facilitate the following discussion.

The following example assumes a single dipole moment, but it is to be understood that extension to a double-layer dipole, which consists of a distribution of multiple such dipole moments, is straight forward. Given a single electric current (i.e. a single dipole moment), a resultant magnetic field at each sensor can be computed based on the Biot-Savart Law, equation Eq. 1, where $\vec{J}(\vec{p})$ is the moment of the electric current including its magnitude and orientation. In this case, $\vec{p}$ is the 3-dimensional (i.e. 3D) position vector of the electric current. Note that this representation of electric current is an approximation by assuming the size (or magnitude) of the current is zero. One can consider that the volume (size, or density) information is included in the moment vector $\vec{J}$. $\vec{B}(\vec{r}_m)$ is the magnetic vector measured by the $m_{th}$ sensor at position $\vec{r}_m = \vec{r}_o + \vec{\delta}_m$, where $r_o$ is the reference point of the sensor plane and δm indicates the offset of the $m_{th}$ sensor with respect to $r_o$. As it would be understood, $\mu_0$ is the magnetic constant.

As it is known in the art, typical MCG systems are capable of measuring only the z component of $\vec{B}$. Thus, to simulate MCG system measurements, one needs to determine the z components of a simulated $\vec{B}$.

From Eq. 1 one may compute $B_z$ (the z component of $\vec{B}$) by means of equation Eq. 2, where $J^1$, $J^2$, $J^3$ represent the three components of the current moment vector $\vec{J}$; $x_p$, $y_p$, $z_p$ represent the three components of the current position vector $\vec{p}$; and $r_m^1$, $r_m^2$, $r_m^3$ represent the three components of the sensor position vector $\vec{r}_m$.

As explained above, a set of high-res P×P MCG images (where P<<M, for example, P may be four times greater than M) are synthesized in a training step. To generate each high-res P×P MCG image, a single electric current with both random moment and random 3D position is defined. The resultant high-res P×P MCG image is computed based on Eq. 2.

Each synthesized high-res MCG image is generated by a single electric current with both random moment and 3D position. Since the magnetic field generated by the heart is very weak ($10^{-12}$ to $10^{-10}$ Tesla), the high-res MCG image is preferably normalized to 0~255 and displayed using a JET color map. In this manner, K high-res MCG training images are generated, i.e. synthesized. All the image vectors are centralized (the mean vector is denoted by μ), and they are stacked into a matrix A. Matrix A thus consists of K columns of P×P vectors. PCA is applied to extract the eigenvectors of matrix A, and thus define an eigenmatrix Σ.

A received sparse M×M MCG image, as measured by an MCG sensor unit, defines a vector g. To restore (i.e. create or define) a high-res MCG image representation of the given sparse M×M measurements (i.e. vector g), one first extracts from the eigenmatrix Σ the rows corresponding to the rows defined by the M×M measurements to form a sub-eigenmatrix Σg. Similarly, vector g's corresponding elements from mean vector μ form a sub-mean vector $\mu_g$. Vector g is then projected to sub-eigenmatrix Σg, and model coefficients $c_g$ are calculated as $c_g=\Sigma_g^+(g_j-\mu_g)$, where $\Sigma_g^+$ is the pseudo inverse of Σg. Finally the original eigenmatrix Σ along with estimated coefficients $c_g$ are used to construct a high-res MCG image vector h, as $h=\Sigma \cdot c_g+\mu$, where h is a P×P vector.

Figure 25:
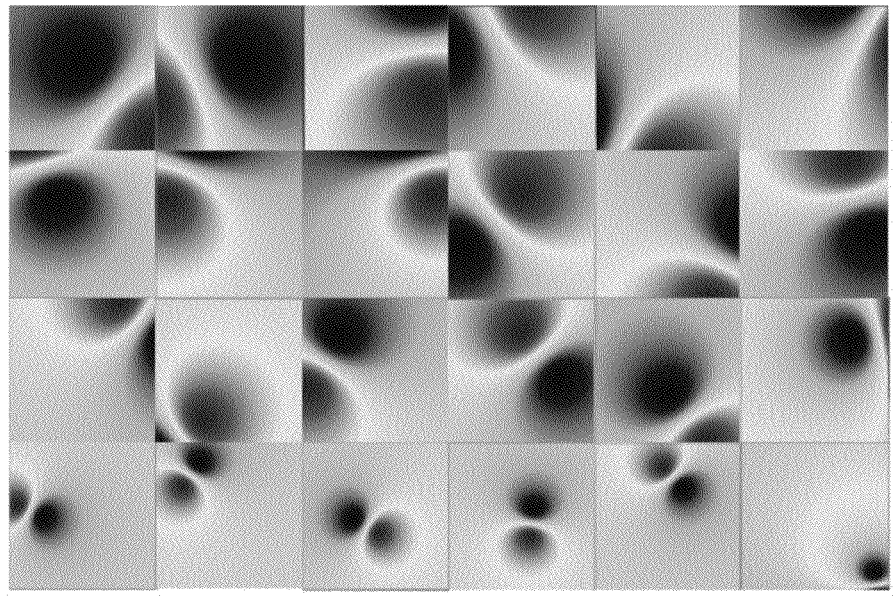
FIG. 25 shows some examples of synthesized training images.

Some examples of synthesized training images are shown in FIG. 25. Four rows of different MCG images (i.e. four 2D MCG images) generated at four respective depths, or layers, are shown. A big variance can be seen between the MCG images with changing depths.

Figure 27:
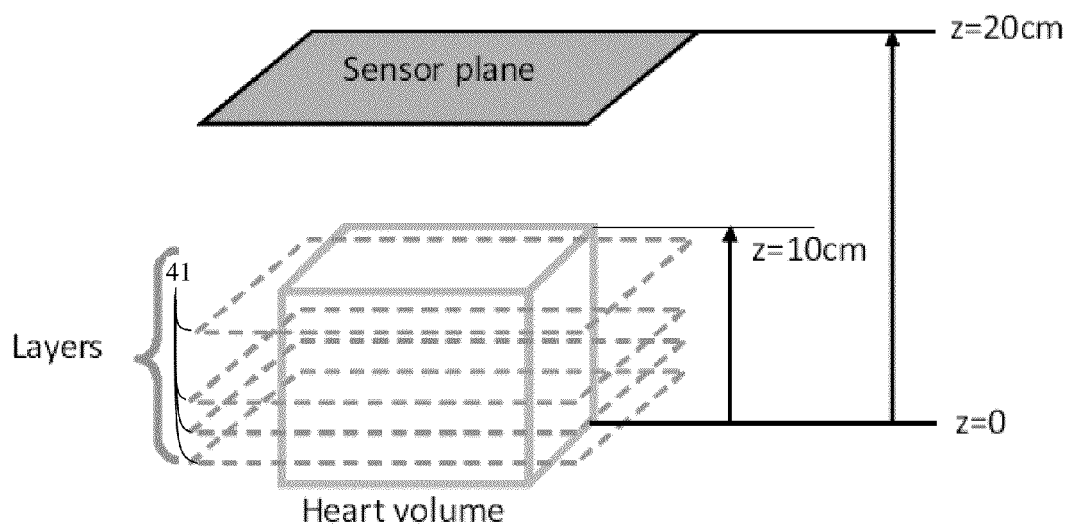
FIG. 27 illustrates depth layers in a heart volume in accord with the present invention.

An illustration of these depth layers 41 is shown in FIG. 27. In the presently embodiment, electric currents are randomly generated at different depth layers 41. It would be too exhaustive to sample every depth to select a set of depth layers. This approach assumes that $B_z$ can be approximated as a linear function of the current depth, as is explained more fully below.

In the present approach, the sensor positions $\vec{r}_m$, the 2D position $(x_p, y_p)$, and the moment $\vec{J}$ the electric current are fixed. $B_z$ is only affected by the depth z of the current. Thus, Eq. 2 can be simplified to Eq. 3, where $a_m$ and $b_m$ are constants but unknowns, c=20 cm is the depth of the sensor, and z is the depth of the current, which varies between 0 to 10 cm within the heart volume bounding box. Preferably, $a_m$ lies in a range from −7.5 to 7.5 cm, and $b_m$ lies in a range from 0 to 112.5 cm.

By applying Taylor expansion to Eq. 3, one obtains Eq. 4. By ignoring $O(\Delta z^3)$, one only needs to prove that $$\frac{d^2}{2dz}B_z^m(z)$$

is close to zero for any possible z and any sensor.

Figure 28:
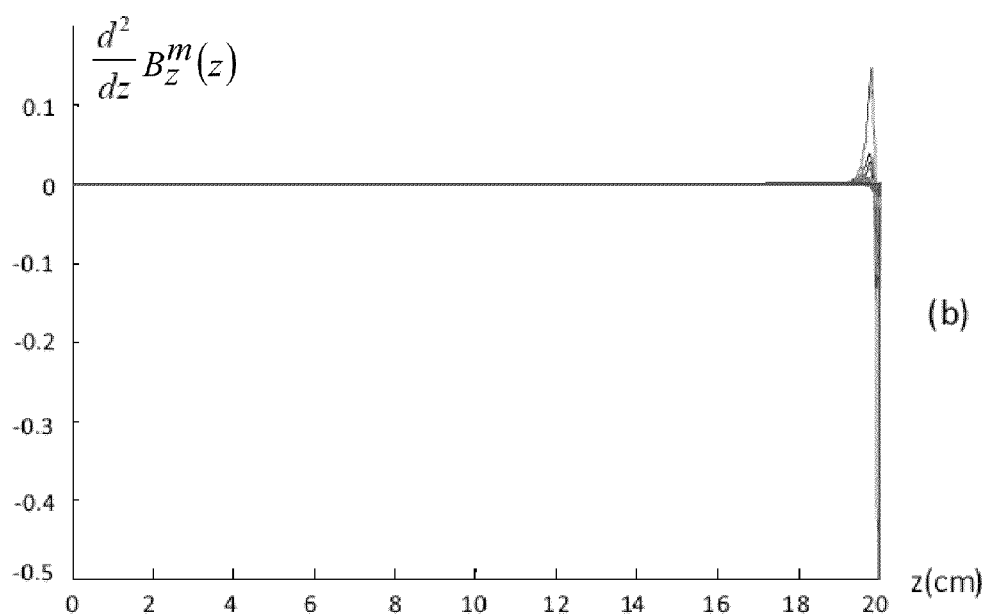
FIG. 28 is a graph of graph of $$\frac{d^2}{2dz}B_z^m(z)$$

A graph of $$\frac{d^2}{2dz}B_z^m(z)$$

versus depth, z, is shown in FIG. 28. More specifically, the graph shows $$\frac{d^2}{2dz}B_z^m(z)$$

in 64 trials with random $a_m$ and $b_m$ in each trial. As shown, $$\frac{d^2}{2dz}B_z^m(z)$$

demonstrates a very small value (close to zero) when z varies from 0 to 10 cm. Therefore, a set of depth layers may be sampled within this depth range, as is illustrated in FIG. 27.

In the present example, one thousand high resolution training MCG image samples were generated in each of 10 evenly distributed depth layers, or levels.

The $B_z$ view and $B_{xy}$ view of the present method of creating a high-res MCG image was then compared with a prior art bicubic interpolation method, as well as with the ground truth images, as is illustrated in FIG. 29. For evaluation purposes, a high-res MCG image reconstructed from the ground truth current based on the Biot-Savart Law is shown. To better simulate physical conditions, 5% uniformly distributed random noise was added to each simulated sensor, and the presently preferred method as well as the prior art bicubic interpolation methods were then applied to the noisy sensor results. As is visually evident from the side-by-side comparison of the three images, the high-res MCG image constructed by means of the presently method more closely matches the ground truth MCG image. Thus the present method achieves a higher level of accuracy in constructing high-res MCG images than the bicubic interpolation method.

With the high-res, training MCG images thus reconstructed, the generated high-res MCG image may be analyzed to identify the location, depth, magnitude and orientation of an electric impulse current that would produce such an image.

As is explained above, true MCG images obtained from observed physical measurements are typically comprised of low-res, 2D MCG maps that do not provide enough information for directly recovering specific electric impulse current information. However, once a high-res MCG image estimation of the low-res, 2D MCG map is constructed, the 2D position of the electric current can be localized as the maximal point of the tangential components of the constructed high-res MCG image. That is, a 2D estimate of the electric current location can be obtained by analyzing the constructed high-res MCG image.

A presently preferred method for improving the localization accuracy is to solve a nonlinear optimization that reconstructs both 3D position and moment of the electric current, i.e. the inverse problem. The higher the accuracy of the estimated high-res MCG image produced by the linear model, the better the initialization for the inverse problem, which helps it converge on the global optimum more quickly. At the same time, the depth, magnitude and orientation of the electric current are also recovered. More specifically, the present method iteratively alternates between two steps (i.e. alternates between estimating a high-res MCG image using the linear model and resolving the inverse problem from the estimated high-res MCG image). The first step estimates the originating position of 3D electric impulse current, and the second step reconstructs its magnitude and orientation based on the estimated originating position. In the estimating of the originating position of 3D electric impulse current, the 2D current location estimated from the model based restoration is used as the initialization. The present method is efficient, accurate and reliable without the need of special assumptions. For the sake of simplicity, the present system/method is illustrated as applied to a single electric impulse current case only. It is to be understood, however, that extension of the present system/method/device to multiple impulse currents is straightforward. It is further to be understood that applying the present method of MCG images generated from double-layer dipoles is equally straightforward since the present method merely calculates an equivalent dipole moment for a given MCG image, irrespective of how that MCG is generated.

The preferred method for generating a 2D estimate from an estimated high-res MCG image is as follows.

Given a high-res MCG image $B_z(i,j)$ ($i=1, 2, \ldots, N$; $j=1, 2, \ldots, N$), the maximal point of the tangential components $B'_{xy}(i,j)$ of $B_z(i,j)$ refers to the 2D position $(x_p, y_p)$ of the electric current. This may be seen in the second row images of FIG. 29. The tangential components of $B_z(i,j)$ may be computed using equation Eq. 5. One now is left with solving the inverse problem.

The inverse problem is to solve both 3D position $\vec{p}$ and moment $\vec{j}$ of the electric current (i.e. the equivalent dipole moment, or current dipole). This approach may be better understood with reference to FIG. 30, where $\vec{r}_o$ is set as the world origin. If $\vec{p}$ is given, the inverse problem becomes a linear one. First, Eq. 1 may be rewritten as Eq. 6, where $\vec{B}^m = \vec{B}(\vec{r}_m)$, $\vec{J} = \vec{J} = \vec{J}(\vec{p})$, and $$\vec{R}_m = \frac{\mu_0}{4\pi} \frac{(\vec{r}_m - \vec{p})}{\|\vec{r}_m - \vec{p}\|^3}.$$

Eq. 6 is then expanded to a matrix form by using a skew symmetric matrix, which results in Eq. 7 of FIG. 26B. In this case, the z component of the magnetic field can be computed as shown in Eq. 8, where $R_m^1, R_m^2$ are x,y components of $\vec{R}_m$. Given M sensors, a linear system is defined as illustrated in equation Eq. 9, where B is a measured M×1 vector, R is a M×2 position matrix that is computed from given $\vec{p}$ and $\vec{\delta}_m$. In the present case, J is a 2×1 unknown vector. When rank(R)≥2 (this holds for the single electric current case with 64 sensors), one can solve a least square solution for J, as illustrated in equation Eq. 10.

Note that by only measuring $B_z$ it is impossible to recover $J^3$. In fact, the magnetic field generated by the z component of the current only propagates along the horizontal direction and never reaches outside of the body. For the following computation, one sets $J^3=0$. Given an estimated current moment $\vec{J} = [J, 0]$, one can update the current position $\vec{p}$.

Eq. 1 is rewritten as equation Eq. 11. One may then let $\alpha = 4\pi/\mu_0$, and $\vec{\epsilon}_0 = \vec{r}_0 - \vec{p}$. $\vec{\delta}_m$ is known for each sensor. One may then apply equation Eq. 12 (see FIG. 26C) to obtain $\alpha \vec{B}^m$. In Eq. 12, let $\vec{\tau}_m = \vec{J} \times \vec{\delta}_m$ and $\vec{\epsilon}_0 = (x_\epsilon, y_\epsilon, z_\epsilon)T$. It is noted that $\vec{\tau}_m$ can be computed given $\vec{J}$. Again, the cross product is removed from Eq. 12 by using a skew-symmetric matrix. Therefor for each sensor m=1:M, one obtains a non-linear equation in terms of $(x_\epsilon, y_\epsilon, z_\epsilon)$, as illustrated in Eq. 13. Letting $F = (f^1; f^2; \ldots; f^M) = 0$, one then solves a least square solution of the nonlinear system F for $\vec{\epsilon}_0$.

Once the offset $\vec{\epsilon}_0$ is obtained, the position matrix R can be updated and J can be recomputed. These iterations are repeated until the algorithm converges. The inverse problem step converges in real time (0.5 seconds on average). Finally $\vec{p} = \vec{r}_0 - \vec{\epsilon}_0$. Since the high-res MCG image only provides an estimate for 2D current position $(x_p, y_p)$, the initial depth z and magnitude $\|\vec{J}\|$ of the electric current are given by equation Eq. 14, where d is the distance between two magnetic poles in the high-res MCG image.

While the invention has been described in conjunction with several specific embodiments, it is evident to those skilled in the art that many further alternatives, modifications and variations will be apparent in light of the foregoing description. Thus, the invention described herein is intended to embrace all such alternatives, modifications, applications and variations as may fall within the spirit and scope of the appended claims.

What is claimed is:

1. A method of constructing a magnetocardiogram (MCG) image of a double-layer dipole, comprising:
   acquiring a magnetic image provided by a sensor unit including a plurality of electromagnetic sensors, each electromagnetic sensor contributing its output data to said magnetic image;
   providing a data processing device to implement the following steps:
   obtaining the magnetic image, said magnetic image being of an image of a magnetic field generated by a double-layer dipole, wherein said double-layer dipole is of an undefined shape, size, depth and orientation;
   submitting said magnetic image to a current dipole constructing system to determine a 3D position and momentum of an electric current in accord with the magnetic image;
   using the Biot-Savart Law to construct said MCG image based on the identified 3D position and moment of the electric current, including:
   assigning the 3D position of the electric current to the geometric center of a single double-layer 2D patch; and
   assigning the geometric center of the single double-layer 2D patch to the position of an equivalent dipole moment of said double-layer dipole, said equivalent dipole moment being characterized by the generation of an electric field substantially similar to that produced by said double-layer dipole; and
   displaying the constructed MCG image.

2. The method of claim 1, further comprising:
   assigning the momentum of the electric current to said equivalent dipole moment.

3. The method of claim 1, wherein said single double-layer 2D patch is an approximation of said double-layer dipole.

4. The method of claim 1, wherein said single double-layer 2D patch is of undefined size.

5. The method of claim 1, wherein said double-layer 2D patch is a distribution of point sources of electric charge having a common polarity.

6. The method of claim 1, wherein said single double-layer 2D patch defines an isochronal activation surface.

7. The method of claim 6, wherein said single double-layer 2D patch is one of two opposing surfaces that define said equivalent double-layer dipole, said equivalent double-layer dipole being equivalent to the double-layer dipole whose magnetic field is represented in said magnetic image.

8. The method of claim 1, wherein the electric field produced by said equivalent dipole moment is substantially similar to that produced by said double-layer dipole when viewed from a distance of multiple times the diameter of the surface of said double-layer dipole.

9. The method of claim 1, wherein:
the magnetic image of the magnetic field generated by a double-layer dipole is a first magnetic image having an M×M resolution of data points; and
the current dipole constructing system determines the 3D position and momentum of an electric current by:
(a) using a high resolution image synthesizer to receive said first magnetic image and produce an intermediate magnetic image, said intermediate magnetic image being a higher resolution image representation of said first magnetic image by:
  (i) accessing a linear model defining a model magnetic image of higher resolution than said first magnetic image, said linear model establishing interpolation patterns between characteristics of the linear model and the M×M data values of the first magnetic image; and
  (ii) producing said intermediate magnetic image by projecting said first magnetic image onto the subspace of the linear model, and establishing coefficients for said intermediate magnetic image in accordance with the linear model and said M×M data values;
(b) submitting the intermediate magnetic image to an electric current localizer for determining the position and momentum of the electric current in accord with said intermediate magnetic image, said electric current localizer evaluating electromagnetic data in an x-y orientation (Bxy) assuming single dipole moment, computing dense Bxy from dense Bz, finding the image maximum in said intermediate magnetic image, and using this determined position information as a starting point in an iterative process for identifying a three-dimensional position vector $\vec{p}$ and momentum vector $\vec{J}$ for said electric current, said three-dimensional position vector $\vec{p}$ and momentum vector $\vec{J}$ defining said position and momentum of the electric current, respectively.

10. The method of claim 9, wherein said linear model is defined by creating a plurality of synthesized magnetic images having the same resolution as said intermediate magnetic image, said synthesized magnetic images being based on simulated electrical impulses within a three-dimensional spatial conductive volume.

11. The method of claim 10, wherein the electrical impulses are double-layer dipoles and said synthesized magnetic images are based on randomly generated double-layer dipoles.

12. The method of claim 11, wherein said randomly generated double-layer dipoles have random depths, shapes and locations within the three-dimensional spatial conductive volume.

13. The method of claim 11, wherein said linear model is created by using principal component analysis (PCA) and said three-dimensional spatial conductive volume is representative of cardiac tissue.

14. The method of claim 10, wherein said synthesized magnetic images are based on randomly generated currents (single dipole moments) within the three-dimensional spatial conductive volume.

15. The method of claim 14, wherein said linear model is created by using principal component analysis (PCA) and said three-dimensional spatial conductive volume is representative of cardiac tissue.

16. The method of claim 10, wherein said interpolation patterns are established by the following steps:
(A) defining the following notation:
N×N dense Bz magnetic field map to form a vector;
M×M sparse measurement to form a vector;
K randomly generated single current dipoles Q;
(B) for each randomly generated current Q, computing an N×N magnetic field map using Biot-Savart equation and stack the resultant image to a vector $f_1$;
(C) repeating step (B) to obtain K samples and getting a data matrix $A = [f_1, f_2, \ldots f_K]$; and
(D) training a PCA model given input data A, to obtain the eigenmatrix $\Sigma_f$.

17. The method of claim 16, wherein said intermediate magnetic image is created by:
given a new dipole and M×M sparse measurements $g_j$, finding the corresponding rows in the eigenmatrix, and denoting a resultant submatrix as $\Sigma_g$;
projecting the sparse measurement to the PCA subspace and computing the coefficients as $c_g = \Sigma_g^+(g_j - g_{mean})$, where $\Sigma_g^+$ is the pseudo inverse of $\Sigma_g$; and
using the computed coefficients and original PCA space to reconstruct the dense magnetic field map Bz, as $f_j = \Sigma_f c_g + f_{mean}$.

18. The method of claim 9, wherein the producing of said intermediate magnetic image includes:
defining the M×M data points as a vector g;
defining the linear model as $\Sigma$;
extracting from $\Sigma$ the row corresponding to each of the M×M data points to form a sub-eigenmatrix $\Sigma_g$;
projecting g onto $\Sigma_g$;
defining the establishment of coefficients as $c_g = \Sigma_g^+(g_i - \mu_g)$, where $\Sigma_g^+$ is the pseudo inverse of $\Sigma_g$, $\mu_g$ are extracted coefficients from a mean vector $\mu$ of linear model $\Sigma$; and
defining the intermediate magnetic image vector h as $h = \Sigma \cdot c_g + \mu$.

19. The method of claim 9, wherein the identifying a three-dimensional position vector $\vec{p}$ and momentum vector $\vec{J}$ for said electric current further includes:
defining said intermediate magnetic image as $B_z(i,j)(i=1, 2, \ldots, N; j=1, 2, \ldots, N)$, the maximal point of the tangential components $B'_{xy}(i,j)$ of $B_z(i,j)$ as referring to the 2D position $(x_p, y_p)$ of the electric current, and the tangential components of $B_z(i,j)$ as $B_{xy}(i,j) = \sqrt{(\partial B_z(i,j)/\partial x)^2 + (\partial B_z(i,j)/\partial y)^2}$; and said iterative process for identifying position vector $\vec{p}$ and momentum vector $\vec{J}$ for said electric current includes:
(a) defining the Biot-Sarvart Law as $\vec{B}^m = \vec{J} \times \vec{R}_m = -\vec{R}_m \times \vec{J}$, where $\vec{B}^m = \vec{B}(\vec{r}_m)$, $\vec{J} = \vec{J}(\vec{p})$ and $$\vec{R}_m = \frac{\mu_0}{4\pi} \frac{(\vec{r}_m - \vec{p})}{\|\vec{r}_m - \vec{p}\|^3};$$

(b) expanding this definition of the Biot-Sarvart Law to a matrix form by using a skew-symmetric matrix:

$$\vec{B}^m = -[\vec{R}_m]_x \vec{J}$$
$$= -\begin{bmatrix} 0 & -R_m^3 & R_m^2 \\ R_m^3 & 0 & -R_m^1 \\ -R_m^2 & R_m^1 & 0 \end{bmatrix} \cdot \begin{bmatrix} J^1 \\ J^2 \\ J^3 \end{bmatrix}$$

where the z component of the magnetic field is computed as:
$$B_z^m = [R_m^2, -R_m^1] \cdot [J^1, J^2]'$$

where $R_m^1, R_m^2$ are x,y components of $\vec{R}_m$, and for said M×M data points one has a linear system:

$$\underbrace{\begin{bmatrix} B_z^1 \\ B_z^2 \\ \vdots \\ B_z^M \end{bmatrix}}_{B} = \underbrace{\begin{bmatrix} R_1^2 & -R_1^1 \\ R_2^2 & -R_2^1 \\ \vdots & \vdots \\ R_M^2 & -R_M^1 \end{bmatrix}}_{R} \cdot \underbrace{\begin{bmatrix} J^1 \\ J^2 \end{bmatrix}}_{J}$$

where B is a measured M×1 vector, R is a M×2 position matrix that is computed from given $\vec{p}$ and $\vec{\delta}_m$, and a lease square solution for J provides an estimateion of J defined as $J=(R^TR)^{-1}R^TB$;

(c) defining the Biot-Sarvart Law as $$\vec{B}^m = \frac{\mu_o}{4\pi} \frac{\vec{J} \times ((\vec{r}_o + \vec{\delta}_m) - \vec{p})}{\left\| (\vec{r}_o + \vec{\delta}_m) - \vec{p} \right\|^3} = \frac{\mu_o}{4\pi} \frac{\vec{J} \times (\vec{\varepsilon}_o + \vec{\delta}_m)}{\left\| \vec{\varepsilon}_o + \vec{\delta}_m \right\|^3}$$

letting $\alpha=4\pi/\mu_0$ and $\vec{\epsilon}_0=\vec{r}_0-\vec{p}$, identifying $\vec{\delta}_m$ as known for each data point to redefining the Biot-Sarvart Law as $$\alpha \vec{B}^m = \frac{\vec{J} \times \vec{\varepsilon}_o + \vec{J} \times \vec{\delta}_m}{\left\| \vec{\varepsilon}_o + \vec{\delta}_m \right\|^3}$$

letting $\vec{\tau}_m = \vec{J} \times \vec{\delta}_m$ and $\vec{\epsilon}_0=(x_\epsilon,y_\epsilon,z_\epsilon)^T$ and computing $\vec{\tau}_m$ from $\vec{J}$, for each data point m=1:M, defining a nonlinear equation in terms of $(x_\epsilon,y_\epsilon,z_\epsilon)$ as $$\alpha B_z^m + \frac{-J^2 x_\varepsilon + J^1 y_\varepsilon + \tau_m^3}{((x_\varepsilon + \delta_m^1)^2 + (y_\varepsilon + \delta_m^2)^2 + (z_\varepsilon + \delta_m^3)^2)^{3/2}} = f^m(x_\varepsilon, y_\varepsilon, z_\varepsilon) = 0$$

letting $F=(f^1; f^2; \ldots; f^m)=0$, and solving a least square solution of the nonlinear system F for $\vec{\epsilon}_0$;

(d) using $\vec{\epsilon}_0$ from step (c) to update the position matrix R and recompute J as in step (b), and iteratively repeating steps (b) and (c) until converges is achieved; and (e) defining the $\vec{p}=\vec{r}_0-\vec{\epsilon}_0$, and defining the initial depth z and magnitude $\|\vec{J}\|$ of the electric current as $$z = d/\sqrt{2.3} \text{ cm}, \quad \|\vec{J}\| = \frac{4\pi d^2 B_z^{max}}{0.385 \, \mu_0}$$

where d is the distance between two magnetic poles in the MCG image.

* * * * *